(12) United States Patent
Borgvall et al.

(10) Patent No.: US 8,329,871 B2
(45) Date of Patent: Dec. 11, 2012

(54) PROCESS OF PURIFYING COAGULATION FACTOR VIII

(75) Inventors: Carin Borgvall, Stockholm (SE); Ulrika Ericsson, Stockholm (SE); Gustav Gilljam, Stockholm (SE); Mats Jernberg, Stockholm (SE); Stefan Winge, Stockholm (SE)

(73) Assignee: Octapharma AG, Lachen (CH)

( * ) Notice: Subject to any disclaimer, the term of this patent is extended or adjusted under 35 U.S.C. 154(b) by 0 days.

(21) Appl. No.: 12/737,230

(22) PCT Filed: Jun. 24, 2009

(86) PCT No.: PCT/EP2009/057883
§ 371 (c)(1),
(2), (4) Date: Feb. 4, 2011

(87) PCT Pub. No.: WO2009/156430
PCT Pub. Date: Dec. 30, 2009

(65) Prior Publication Data
US 2011/0160435 A1   Jun. 30, 2011

Related U.S. Application Data

(60) Provisional application No. 61/129,402, filed on Jun. 24, 2008.

(30) Foreign Application Priority Data

Jun. 24, 2008   (EP) .................................... 08158893

(51) Int. Cl.
*C07K 1/16* (2006.01)
*C07K 1/20* (2006.01)
*C07K 1/18* (2006.01)

(52) U.S. Cl. ......... 530/383; 424/520; 424/529; 424/530
(58) Field of Classification Search .................. None
See application file for complete search history.

(56) References Cited

U.S. PATENT DOCUMENTS

| 5,605,884 A | 2/1997 | Lee et al. |
| 5,831,026 A | 11/1998 | Almstedt et al. |

FOREIGN PATENT DOCUMENTS

| AU | 687 451 | 2/1998 |
| EP | 1 707 634 | 10/2003 |
| WO | WO 94/08686 | 4/1994 |
| WO | WO 2005/082483 | 9/2005 |
| WO | WO 2005/121163 | 12/2005 |
| WO | WO 2008/008975 | 1/2008 |
| WO | WO 2009/007451 | 1/2009 |

OTHER PUBLICATIONS

Bhattcharyya et al. "Recombinant Factor VIII for Haemophilia An Overview of Production Technologies." CRIPS, vol. 4, No. 3, Jul.-Sep. 2003, pp. 2-8.
Eriksson et al. "The Manufacturing Process for B-Domain Deleted Recombinant Factor VIII." Seminars in Hematology, vol. 38, No. 2, suppl. 4, Apr. 2001, pp. 24-31.
Farrugia. "Biotechnology and the Plasma Fractionation Industry—The Impact of Advances in the Production of Coagulation Factor VIII." Biotechnology, vol. 3, No. 1, Feb. 1993, pp. 16-20.
Parti et al. "In vitro stability of recombinant human factor VIII." Haemophilia, vol. 6, 2000, pp. 513-522.
Wang et al. "Coagulation factor VIII: structure and stability." International Journal of Pharmaceutics, vol. 259, 2003, pp. 1-15.
Burton et al. "Salt-independent adsorption chromatography: new broad-spectrum affinity method for protein capture." Biochemical and Biophysical Methods, vol. 49, 2001, pp. 275-287.
Johansson et al. "Preparation and characterization of prototypes for multi-modal separation aimed for capture of positively charged biomolecules at high-salt conditions." Journal of Chromatography A, vol. 1016, 2003, pp. 35-49.
Johansson et al. "Preparation and characterization of prototypes for multi-modal separation media aimed for capture of negatively charges biomolecules at high salt conditions." Journal of Chromatography A, vol. 1016, 2003, pp. 21-33.
Xindu et al. "Liquid chromatography of recombinant proteins and protein drugs." Journal of Chromatography B, vol. 866, 2008, pp. 133-153.
Arakawa et al. "Induced binding of proteins by ammonium sulfate in affinity and ion-exchange column chromatography." vol. 70, 2007, pp. 493-498.

*Primary Examiner* — Kagnew H Gebereyesus
(74) *Attorney, Agent, or Firm* — Jacobson Holman PLLC

(57) ABSTRACT

A process of purifying or enriching coagulation FVIII employing chromatography comprising the steps of providing a fraction containing FVIII in an aqueous solution having a high ionic strength; contacting the fraction containing FVIII with a multimodal resin; optionally washing the multimodal resin having FVIII adsorbed with an aqueous washing buffer; eluting FVIII containing fractions by an aqueous elution buffer comprising at least one amino acid which is positively charged at pH 6 to 8; and optionally collecting FVIII containing fractions in purified or enriched form.

22 Claims, 11 Drawing Sheets

Lane    1    2

VIIISelect Scheme

Capto Adhere Scheme

Lane   1   2   3   4     5   6   7   8   9

170 kDa 90 kDa
80 kDa

Lanes:   1   2   3        4

FIG. 8

Cell suspension (2-3e7 Cells / mL)
↓
Salting
↓
Cell separation
↓
DNA reduction (Q-membr.)
↓
Capture Step
(Capto MMC)
↓
Sp Seph FF
↓
DNA reduction (Q-membr.)
↓
S/D-treatment
↓
VIIISelect Affinity ligand
↓
Q-Seph FF
↓
GF-Eluate

PROCESS OF PURIFYING COAGULATION FACTOR VIII

This is a national stage of PCT/EP09/057883 filed Jun. 24, 2009 and published in English, which has a priority of European no. 08158893.1 filed Jun. 24, 2008, claiming benefit of U.S. provisional application No. 61/129,402, filed Jun. 24, 2008, hereby incorporated by reference.

The present invention pertains to a process of purifying coagulation factor VIII (abbreviated as FVIII) and a fraction containing FVIII obtainable by the process of the invention.

BACKGROUND OF THE INVENTION

Hemophilia is a group of hereditary genetic disorders that impair the body's ability to control blood clotting or coagulation. In its most common form, Hemophilia A, clotting FVIII is deficient, Hemophilia A occurs in about 1 in 5,000-10,000 male births. The FVIII protein is an essential cofactor in blood coagulation with multifunctional properties. The deficiency of FVIII can be treated with plasma-derived concentrates of FVIII or with recombinantly produced FVIII. The treatment with FVIII concentrates has led to a normalized life of the hemophilia patients. Historically, Hemophilia A has been treated with FVIII originating from human blood plasma. In blood plasma, under normal conditions, the FVIII molecule is always associated with its cofactor; von Willebrandt factor (vWf), which stabilizes the FVIII molecule from different forms of degeneration.

Plasma derived FVIII products occur on the market with different purities and with more or less amounts of vWf present. Commonly, products with low amount of vWf contain added human albumin and or other stabilizers including increased salt concentration to stabilize the FVIII molecule). The methods used to purify FVIII were normally a combination of different precipitation methods such as cryo precipitation, aluminum hydroxide precipitation etc. and chromatography steps mainly ion exchange, affinity and gel filtration steps.

In order to improve FVIII products affinity chromatography was employed, which effectively removed contaminants to a high degree of FVIII purity including the possibility to reduce also vWf (Farrugia et al., Biotechnology and plasma fractionation industry; The impact of advances in the production of coagulation FVIII. Biotechnology, Vol. 3, No. 1, February 1993). The disadvantage with immuno affinity chromatography was that it is relatively expensive and that the monoclonal antibodies used as affinity ligands, where of animal origin.

In the mid 80's there where some virus transmissions associated with plasma derived FVIII products. Even if this problem was solved through implementation of specific virus reduction steps, this was the starting point of the development of recombinant FVIII products (rFVIII). In the 90's, the first rFVIII product was marketed and up to date there are three different rFVIII products (two full length molecules and one B-domain deleted molecule in which an inactive part of the FVIII molecule has been removed to increase the productivity of the host cell (Eriksson et al., The manufacturing process for B-domain deleted recombinant FVIII. Seminars in Hematology, Vol 38, No 2, Suppl. 4 (April), 2001: pp 24-31)) with a high degree of purity (all without vWf).

The purification methods used to purify the rFVIII, all were a combination of different chromatography techniques (ref. Bhattacharyya et al., Review article; Recombinant FVIII for Haemophilia "An overview of production technologies". CRIPS Vol. 4, No. 3, July-September 2003). One was the known immuno affinity technique (even if there are products solving this, for example with peptide affinity (Kelly et al., Development and validation of an affinity chromatography step using a peptide ligand for cGMP production of FVIII.) or a yeast derived antibody fragment (VIIISelect FVIII affinity resin—GE Healthcare, Cat. No. 17-5450 presently are entering the market) as used for the plasma FVIII.

As vWf is absent in all rFVIII products, certain measures have to be taken to stabilize the FVIII molecule against loss of activity (aggregation, proteases, surface adsorption etc.). In one of the products, a chelating agent (EDTA etc.) is added to protect FVIII against degeneration of metallo proteases (U.S. Pat. No. 5,831,026). To add albumin, aprotinin, insulin or even to co-express rFVIII with vWf (and remove it down stream in the purification cycle) are strategies which have been performed to increase the stability of the rFVIII molecule (ref. Bhattacharyya et al., Review article; Recombinant FVIII for Haemophilia "An overview of production technologies". CRIPS Vol. 4, No. 3, July-September 2003).

Another strategy (to maintain a process free of mammalian additives and chelating agents) is described in EP-A-1 707 634, where a combination of increased amounts of salts, contribute to the stability and high recovery of the rFVIII product (Wang et.al, Coagulation FVIII, structure and stability. International Journal of Pharmaceuticals, 259 (2003), 1-15.). However, this technique has a certain disadvantage. For example, the relatively high salt content makes it not suitable to process directly to an ion exchanger without dilution (and possible destabilization Parti et al., In vitro stability of recombinant FVIII. Haemophilia (2000), 6, 513-522. Biotechnology and Bioengineering, Vol. 87, No. 3, Aug. 5, 2004.).

WO-A-2009/007451 discloses a purification method of FVIII using a mixed-mode or multimodal resin. The purification method is based on contacting FVIII protein with a multimodal or mixed-mode resin containing ligands which comprise a hydrophobic part and a negatively charged part and eluting said FVIII protein with an elution buffer containing at least 1.5 M salt and at least 40% (w/v) of ethylene glycol, propylene glycol or a mixture thereof, and calcium ions.

EP-A-1707634 discloses a method for isolation of recombinantly produced proteins i.a. by various methods such as immuno-affinity chromatography, affinity chromatography, protein precipitation, buffer exchanges, ionic exchange chromatography, hydrophobic interaction chromatography, mixed-mode hydrophobic/ion exchange chromatography media, chelating chromatography, carbohydrate affinity like lectin or heparin affinity chromatography, size-exclusion chromatography, electrophoresis, dialysis, different precipitation agents such as polyethylene glycol, ammonium sulphate, ethanol, hydroxy apatite adsorption, filter membrane adsorption, ligands coupled to magnetic particles etc. However, it is identifying particular chromatographic purification steps.

WO-A-2005-082483 discloses a process for the purification of antibodies from one or more impurities in a liquid, which process comprises contacting said liquid with a first chromatography resin comprised of a support to which multimodal ligands have been immobilised to adsorb the antibodies to the resin, wherein each multi-modal ligand comprises at least one cation-exchanging group and at least one aromatic or heteroaromatic ring system. An eluant is added to release the antibodies from the resin and the eluate is contacted with a second chromatography resin.

WO-A-2005/121163 discloses a process for the isolation of one or more proteins from a protein solution. The process comprises the steps of providing a protein solution comprising one or more specific proteins and having a preset pH and a preset ionic strength or conductivity, applying the protein solution to a packed bed or expanded bed column comprising an adsorbent, and obtaining one or more proteins fromt he column, wherein the protein solution has been supplemented with an alcohol.

DESCRIPTION OF THE INVENTION

One object of the invention was to avoid the drawbacks of the purification processes of prior art by providing a novel process. Another object of the invention was to provide a process of purifying FVIII in particular from sources having high salt content, in particular as they are used in the manufacturing of recombinant FVIII.

This is accomplished by a process of purifying coagulation FVIII in a purification sequence employing chromatography wherein at least one chromatography is performed using a multimodal resin. The term "multimodal resin" as used herein means a chromatographic material having a support and moieties bound to the support which moieties interact with chemical groups of the substances to be separated. In a particular embodiment of the invention the multimodal resin comprises moieties bound to a matrix and the moieties are able to interact with FVIII in a mixture by ionic interactions and other types of interactions such as hydrogen bonding and/or hydrophobic interaction.

BRIEF DESCRIPTION OF THE DRAWINGS

FIGS. 8, 9, and 10 are flow charts of embodiments of the process according to the invention.

Figure 1:
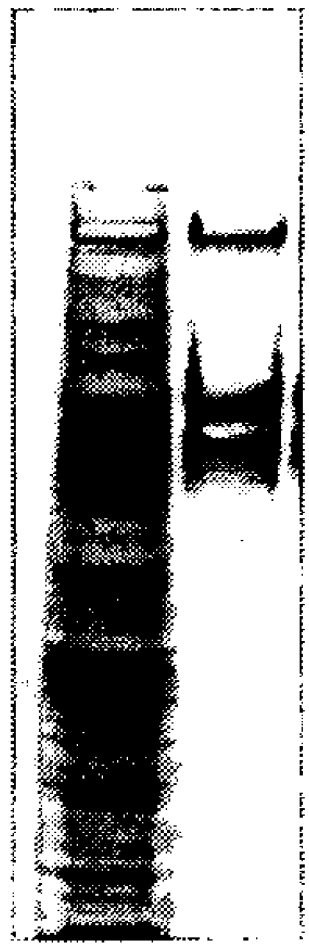
FIGS. 1, 2, 3, 4, 5a, 5b, 6, and 7 show pictures of silver-stained SDS-PAGE gel electrophoresis.

According to the invention a process is provided of purifying or enriching coagulation FVIII employing chromatography comprising the steps of providing a fraction containing FVIII in an aqueous solution having a high ionic strength; contacting the fraction containing FVIII with a multimodal resin; optionally washing the multimodal resin having FVIII adsorbed with an aqueous washing buffer; eluting FVIII containing fractions by an aqueous elution buffer comprising at least one amino acid which is positively charged at pH 6 to 8; and optionally collecting FVIII containing fractions in purified or enriched form.

Multi modal (or mixed mode) chromatography is a tool for purifying proteins. Described in, for example, Manufacturer data sheet GE Health Care (11-0035-45AA) Capto Adhere, Manufacturer data sheet GE Health Care (28-9078-88AA) Capto MMC and patent application EP 07114856.3 "A process for the isolation and purification of a target protein, free of prion proteins".

The techniques have certain advantages and disadvantages. One advantage being the possibility to bind proteins within a higher salt concentration, compared to the more often used ion exchange chromatography. A disadvantage is that the elution often includes relatively harsh conditions like for example pH below or above neutral pH, alone or in combination with other elution parameters. FVIII is a relatively unstable protein, for example in regard of pH values outside the neutral value; pH 6-8 (Wang et. al, Coagulation FVIII, structure and stability. International Journal of Pharmaceuticals, 259 (2003), 1-15.). The invention solves this problem by mild elution conditions in a pH range about neutral which retains the activity of the FVIII molecule and facilitates the use of multi modal chromatography in combination with the stabilisation effects of the increased salt concentration, described in for example in EP-A-1 707 634.

According to one embodiment of the invention the multi modal chromatography may be performed in a chromatographic column. This may be regarded as a first capture step. The process of the invention can also be performed in a batch mode. The present invention also facilitates a process of purification without addition of human or animal derived stabilizing additives and the use of a whole process which is absent thereof (monoclonal antibody based immuno affinity resins). The use of the multimodal resin, in particular as capture step, facilitates also a higher binding capacity in comparison with conventional ion exchangers, which results in a more concentrated product eluate from the step, which is of advantage for the product stability.

The process of the invention is typically related with the purification of recombinant FVIII (FVIII), in particular B-domain deleted recombinant FVIII.

FVIII Typically the solution comprises FVIII in a high salt concentration solution corresponding to a conductivity of from about 25 to about 200 mS/cm at 25° C.

In another embodiment of the invention FVIII is applied to the multimodal resin and after binding to the multimodal resin subsequently eluted with a suitable buffer.

After application of the mixture comprising FVIII and binding FVIII to the multimodal resin, the FVIII molecule is eluted from the multimodal resin using an elution buffer comprising at least one amino acid which is positively charged at a pH 6 to 8, in particular the amino acid which is positively charged at a pH of 6 to 8 is lysine, arginine and/or histidine.

Additionally, the buffer may be comprising at least one hydroxyl group containing organic compound such as an alcohol, at least one amino group containing organic compound such as an amino acid, a source providing $Ca^{2+}$ ions, at least one compound for regulating the ionic strength of the buffer such as inorganic salts e.g. NaCl in particular in concentrations $\leq$1M, a non-ionic detergent and a buffering substance to regulate the pH from about 6 to about 8 in particular to about a neutral value.

In a further embodiment of the process of the invention the alcohol can be selected from the group of methanol, propanol and ethylene glycol; the amino acid can be selected from the group of arginine, lysine and histidine; the source providing $Ca^{2+}$ can be $CaCl_2$; the inorganic salts can be selected of the group of KCl and NaCl; the non-ionic detergent can be selected from the group of Tween 20, Tween 80 and Pluronic F68; the buffering substance can be selected from the group of sodium citrate, histidine, HEPES, MES and sodium acetate at a pH between 6-8.

Particularly, the concentration of the amino acid which is positively charged at a pH 6 to 8 is present in an amount of at least >0.4M, in particular >0.5M. If concentrations larger than 1M of the particular amino acid is used, this does not lead to further advantages. Typically, the amount of arginine is in a range of from about 0.4M to about 1.0M, in particular in a range from about 0.7M to about 0.9M. The hydroxyl group containing organic compound such as an alcohol e.g. ethylene glycol is in particular present in amounts of from 0% (v/v) to 30% (v/v), in particular from about 5% to 15%. The calcium ion concentration should be in the range of from 0.0001M to about 0.1M, in particular from about 0.001M to about 0.03M. The concentration of the compound for regulating the ionic strength of the buffer should be in the range to provide a conductivity from about 15 to about 200 mS/cm at 25° C. The amount of non-ionic detergent is typically in the range from about 0.001% to 1%.

In an embodiment the process of the invention a wash buffer is applied to the multimodal resin. This can be used to wash away contaminants and retain FVIII, before the FVIII is released.

In a further embodiment the process of the invention the "multimodal" chromatography resin contains at least one of the following moieties:
  i) a positively charged N-Benzyl-N-methyl ethanolamine ligand
  ii) a negatively charged 2-(benzoylamino) butanoic acid ligand,
  iii) a phenylpropyl ligand,
  iv) a N-hexyl ligand,
  v) a 4-Mercapto-Ethyl-Pyridine ligand,
  vi) a 3-((3-methyl-5-((tetrahydrofuran-2-ylmethyl)-amino)-phenyl)-amino)-benzoic acid ligand or combinations thereof.

In particular, in the process of the invention the "multimodal" chromatography resin is selected from the following commercially available resins HEP Hypercel™; PPA Hypercel™; Capto Adhere™; Capto MMC™; MEP Hypercel™.

In another embodiment the process of the invention, the multimodal chromatography step is combined with a FVIII affinity chromatography step wherein the affinity is provided by a protein ligand such as an antibody fragment which is expressed in yeast.

According to the process of the invention the purification sequence further comprises pathogen removal/inactivation steps comprising a chemically based inactivation step, a size based removal step, chromatography steps or combinations thereof which steps are based on different physiological properties directed to the pathogen to be removed.

In a particular embodiment the process of the invention the purification sequence further comprises the following steps:
  i. the use of an anionic membrane such as Sartobind Q in particular for DNA reduction;
  ii. a cation multimodal resin such as Capto MMC;
  iii. a cation exchanger resin such as SP Sepharose FF;
  iv. the use of a secondary anionic membrane such as Sartobind Q in particular for further DNA reduction;
  v. a chemically based inactivation step for lipid enveloped viruses in particular the solvent/detergent-inactivation employing tri-n-butyl phosphate and Triton X-100 as disclosed in EP-A-131 740;
  vi. an affinity resin based on a protein ligand expressed in yeast; such as VIIISelect or an anion multimodal chromatography resin such as Capto Adhere;
  vii. a pathogen filtration removal step with a mean pore size of about 20 nm such as Planova 20N;
  viii. an anion exchanger resin such as Q Sepharose FF;
  ix. a size exlusion chromatography resin such as Superdex 200 pg.

In particular, in the process of the invention the elution conditions of the cation exchange step are based on $Ca^{2+}$-ions, concentration ranging from 0.15-0.25 M and the total conductivity of the elution buffer not increasing 25 mS/cm at 25° C.

If the process of the invention is employed, the purity of the obtainable product is >4000 IU/mg, after the last purification step preferably >9000 IU/mg and more preferably >10 000/mg protein and <1 000 pg/1000 IU FVIII, preferably <100 pg/1000 IU FVIII and more preferably <10 pg/10001 U FVIII in regard of DNA contamination.

Therefore also a composition of matter is subject of the invention which composition of matter is comprising a purified recombinant FVIII obtainable by the process according to the invention (without the addition or use of any human or animal additatives like albumin or monoclonal antibody based immunoaffinity ligands).

FIG. 8 shows a flow sheet of a process according to the invention wherein the capture step is performed on a multimodal resin. A cell suspension is processed by adding salt, separation of the cells followed by a DNA reduction step, preferably on a Q membrane. The Q membrane (for example Sartobind Q from Sartorious) is a strong basic anion exchanger with quaternary ammonium groups as anion exchange moiety. Within specific ranges of pH and conductivity the Q membrane binds specifically DNA, whereas the product (and host cell proteins) remains in the flow through. In opposite to conventional ion exchange column chromatography, the charged ligand is bound to a membrane support which facilitate a high throughput and easy-to-use. The capture step comprises the method of the invention using the multimodal resin. The capture step is followed by a separation on a cation exchanger, SP Sepharose FF™ (GE HealtCare) followed by a further DNA reduction on a Q membrane. A virus inactivation treatment by the solvent detergent method (S/D method) as for example disclosed in EP-A-131740 is performed and a further purification step on e.g. VIII Select™ affinity resin. A further concentration/polishing step is performed on an anion exchanger column, for example on Q Sepharose FF™ (GE HealtCare). The concentrated product is thereafter processed on a gelfiltration column (e.g. Superdex 200 p.g.™ (GE HealtCare)) to exchange buffer and remove potential aggregates and fragments. The resulting product, GF eluate, is collected. The respective steps are explained in more detail in the Examples.

Figure 9:
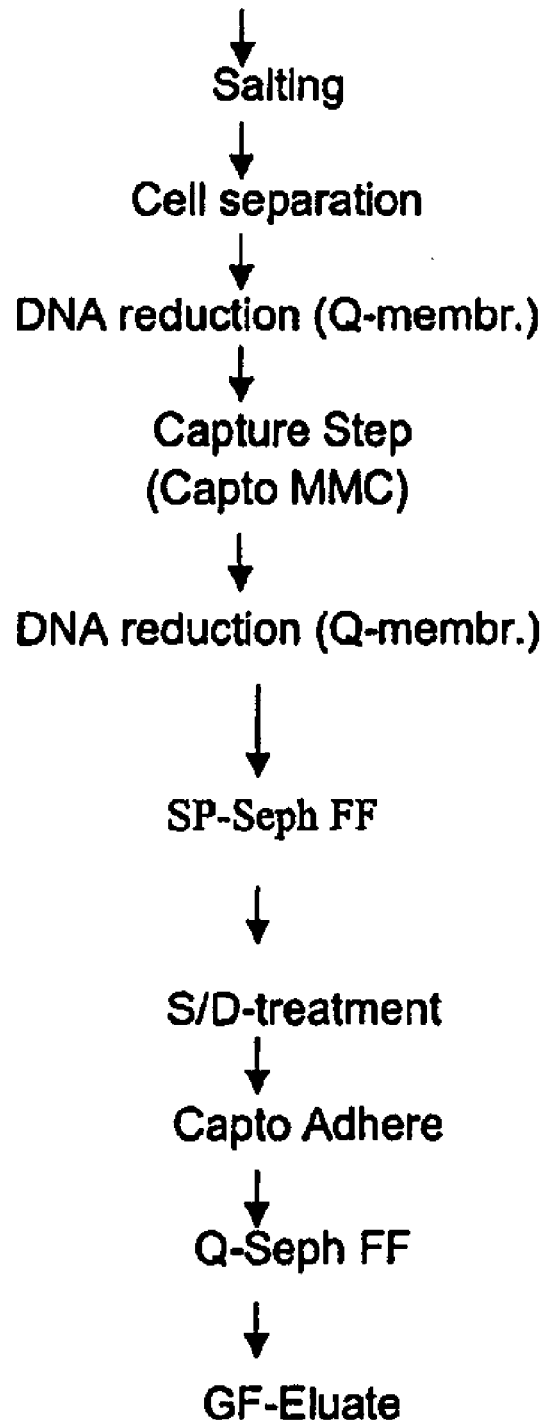
Figure 10:
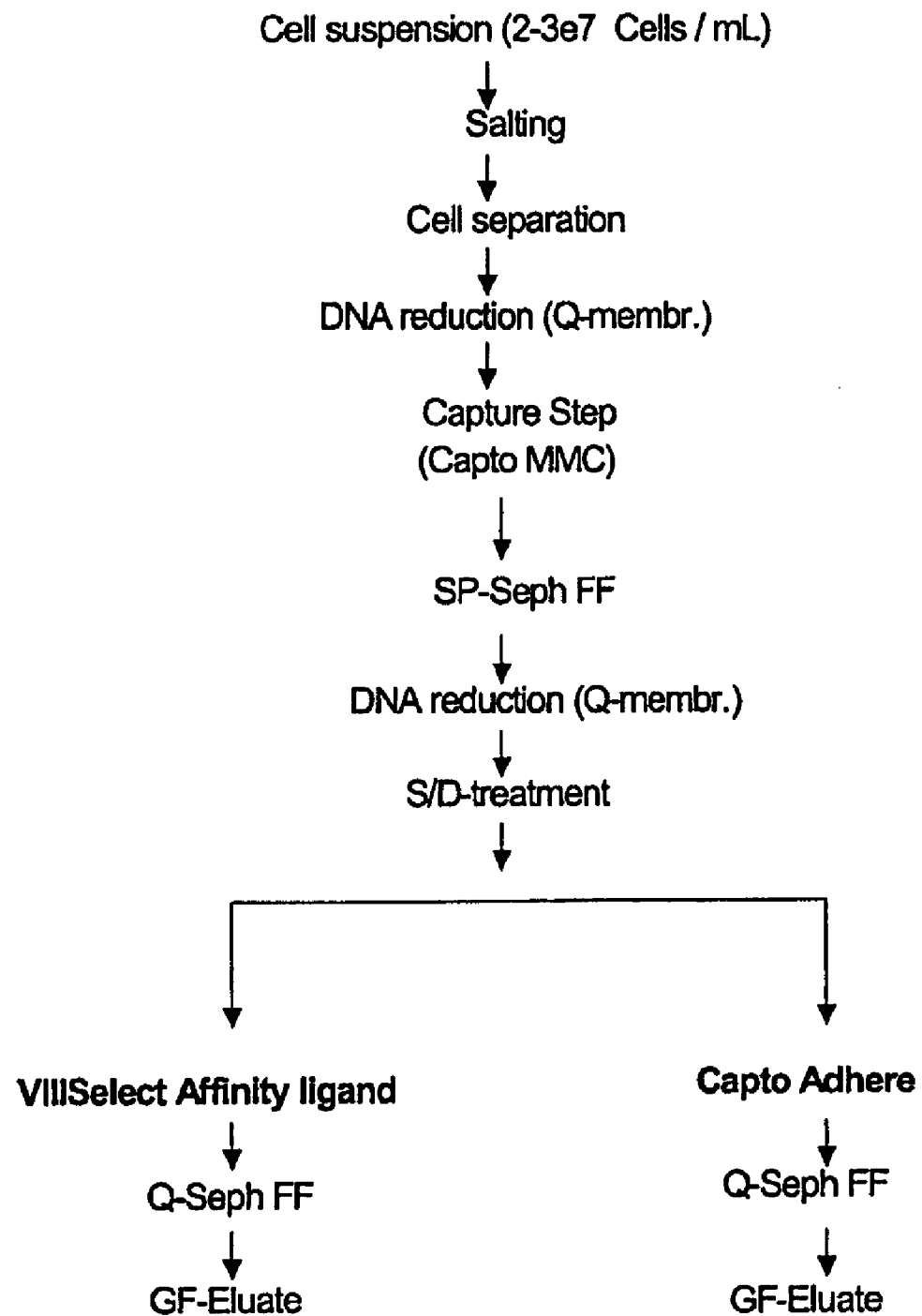

Each of FIGS. 9 and 10 shows an alternative embodiment wherein the specific affinity step (VIIISelect™ (GE HealtCare)) as described in FIG. 8, is replaced by a multimodal chromatography; Capto Adhere™ (GE HealtCare). Surprisingly, the purification sequence, as described in FIG. 9, exerted the same purity as the purification sequence described in FIG. 8 (including the specific antibody based affinity step). This result was repeated with the same starting material, as described in FIG. 10. This shows the ample potential of using the multimodal purification technique more than once (both in the capture step; Capto MMC™ (GE HealtCare) and in a further downstream purification step with Capto Adhere™ (GE HealtCare) as described in FIGS. 9 and 10) using the specific elution conditions for FVIII, according to the invention.

The invention is further described by the following non-limiting examples.

EXAMPLES

In all examples the actual value of M (Molar) is mol/Kg (i.e. 10 gram of salt is added to 1000 gram of water—not 10 gram of salt is added water up to 1000 mL)

Example 1

Production of FVIII Containing Cell Suspension

Cells

The cell line used is a derivative of human embryonic kidney cell 293 (HEK 293), which was adapted to serum-free growth. This host, HEK 293F, was stably transfected with an expression cassette carrying the gene for B-domain deleted human FVIII under control of a strong promoter (EP-A-1 739 179).

Cultivation Method

The cells were cultivated in serum-free medium in general equipment and according to general methods well known in the art, for example shaken or stirred cultures in t-flasks, shaker flasks and bioreactors (disposable systems and conventional stirred tanks) run as batch, fed-batch, perfusion or continuous chemostat cultures (Freshney, R I (2000), Culture of animal cells: a manual of basic technique, 4$^{th}$ ed, Wiley-Liss; Spier, R E ed (2000), Encyclopedia of cell technology, Wiley, New York; Enfors, S-O and Häggström, L (2000), Bioprocess technology: fundamentals and applications, Högskoletryckeriet, Royal Institute of Technology, Stockholm; Vinci, V A and Parekh, S R (2003), Handbook of industrial cell culture: mammalian, microbial, and plant cells, Humana Press, USA). Typically, perfusion of medium was used to increase cell numbers and product titers beyond standard batch culture levels. The product yield and the amount of host cell proteins differ depending on the cultivation mode:

the product titre will typically increase with cell numbers the total protein content and DNA content will typical increase with cell numbers the total protein content and DNA content can also increase with culture longevity batch cultures accumulate protein and DNA; nothing is externally added, nothing is removed perfusion processes rinse cell cultures from metabolites, protein, DNA and other impurities; filters or cell centrifuges were typically used for cell retention.

Since the recombinant product is associated with the cells, the cell suspension is the harvest. The properties of the harvest (product titres and impurities as mentioned above) differ depending on the cultivation mode used.

Example 2

Producing the Cell Free FVIII Starting Material

The cell free FVIII starting material for the chromatographic purification, was achieved as follows. A stock solution of sodium chloride and calcium chloride was added to the cell-suspension, produced according to example 1, to give final concentrations of 0.3M and 30 mM respectively, and a conductivity of 30-40 mS/cm at 25° C. The solution was mixed for about 30 minutes, where after the cells were removed by centrifugation and followed by a filtration step to remove any remaining cell debris (to inhibit clogging of the following column steps).

Example 3

Elution Conditions for Multimodal Cation Resin Capto MMC

The following series of experiments were performed to compare different elution conditions on the multimodal cation resin Capto MMC.

Example 3a

Evaluation of Different Salt Concentration and pH to Elute FVIII from Capto MMC Resin (Reference Example)

Column and Resin

The Capto MMC resin was packed to a bed height of 10 cm in a C10/20 column (1 column volume (CV)=8 mL). The Capto MMC resin was obtained from GE Healthcare (Cat. No. 17-5317).

Starting Material

The starting materials used were a protein solution containing rFVIII, obtained as described in example 2.

Equilibration Buffer 0.01 M L-Histidine, 0.01 M CaCl$_2$, 0.3 M NaCl, 0.02% w/w Polysorbate 80, pH 7.0, conductivity 31±3 mS/cm at 25° C.

The column was equilibrated with equilibration buffer followed by loading of the starting material with a flow rate of 5 mL/min. FVIII bound to the resin during these buffer conditions (no FVIII could be detected in the flow through). The resin was thereafter subjected to different elution conditions as described in Table 1 and the resulting amount of FVIII coming out from the column where analyzed with a FVIII:C method and calculated in % in relation to the applied amount of FVIII.

TABLE 1

| Elution conditions | Eluted volume (CV) | FVIII:C found in eluate, (%) |
| --- | --- | --- |
| 0.1M NaCl, pH 6.5* | 10 | 0 |
| 0.3M NaCl, pH 7.0* | 90 | 0 |
| 1M NaCl, pH 6.5** | 20 | 0 |
| 2M NaCl, pH 6.5** (OgH07-626) | 15 | 0 |

*Elution buffers included 0.01M L-Histidine, 0.01M CaCl$_2$ and 0.02% w/w Polysorbate 80
**The eluting buffer included 0.05M L-Histidine, 0.05M CaCl$_2$ and 0.02% w/w Polysorbate 80

Conclusion Reference Example 3a

As can be seen in table 1, the binding of FVIII to the Capto MMC column, is not an ionic interaction.

Reference Example 3b, Evaluating Elution Conditions for Capto MMC, Different NaCl Concentration with 50% Ethylene Glycol Constant Column and Resin The Capto MMC resin was packed to a bed height of 2 cm in a XK16/20 column (1 column volume (CV)=4 mL). The Capto MMC resin was obtained from GE Healthcare (Cat. No. 17-5317).

Starting Material

The starting materials used were a protein solution containing rFVIII, obtained as described in example 2.

Equilibration Buffer 0.01 M L-Histidine, 0.01 M CaCl$_2$, 0.3 M NaCl, 0.02% w/w Polysorbate 80, pH 7.0, conductivity 31±3 mS/cm at 25° C.

The column was equilibrated with equilibration buffer followed by loading of the starting material with a flow rate of 1 mL/min. FVIII bound to the resin during these buffer conditions (no FVIII could be detected in the flow through). The resin was thereafter subjected to different elution conditions as described in Table 2 and the resulting amount of FVIII coming out from the column were analyzed with a FVIII:C method and calculated in % in relation to the applied amount of FVIII.

TABLE 2

| Elution conditions* | Eluted volume (CV) | FVIII:C found in eluate, (%) |
|---|---|---|
| 0.5M NaCl + 50% Ethylene glycol pH 6.5 | 3 | 23 |
| 1M NaCl + 50% Ethylene glycol pH 6.5 | 6 | 52 |
| 1.5M NaCl + 50% Ethylene glycol pH 7.5 | 4 | 73 |
| 1.5M NaCl + 50% Ethylene glycol pH 6.5 | 2 | 82 |
| 2.5M NaCl + 50% Ethylene glycol pH 6.5 | 3 | 84 |

*All elution buffers included 0.02M L-Histidine, 0.02M CaCl$_2$ and 0.02% w/w Polysorbate 80

Conclusion Reference Example 3b

As can be seen in table 2, the binding of FVIII to the Capto MMC column can be inhibited by a combination of ethylene glycol and NaCl. 50% Ethylene glycol is commonly used as elution buffer for conventional protein based affinity resins. The elution of FVIII is improved if ethylene glycol is combined with an increased sodium chloride concentration up to 1.5M. Two different pH tested (pH 6.5 and 7.5) do not change the FVIII recovery, indicating that the pH cannot be used as an elution parameter for FVIII, within the stability limits for the protein (approximately. 6-8). An elevation of the NaCl concentration to 2.5M did not improve the recovery of FVIII:C in the eluate.

Example 3c

Variation of Arginine as an Elution Component for Capto MMC

Column and Resin
The Capto MMC resin was packed to a bed height of 8 cm in a Tricorn 5/100 column (1 column volume (CV)=1.6 mL). The Capto MMC resin was obtained from GE Healthcare (Cat. No. 17-5317-10).
Starting Material
The starting materials used were a protein solution containing rFVIII, obtained as described in example 2.
Equilibration Buffer
0.01 M L-Histidine, 0.01 M CaCl$_2$, 0.3 M NaCl, 0.02% (w/w) Polysorbate 80, pH 7.0, conductivity 31±3 mS/cm at 25° C.
The column was equilibrated with equilibration buffer followed by loading of the starting material with a flow rate of 0.6 mL/min. FVIII is bound to the resin during these buffer conditions (no FVIII could be detected in the flow through). The resin was thereafter subjected to different sequential elution conditions (approximately 10 column volume (CV) each) as described in Table 3 and the resulting amount of FVIII eluting from the column where analyzed with FVIII:C method and calculated in % in relation to the applied amount of FVIII.

TABLE 3

| Elution conditions* | FVIII found in Eluate, (%) |
|---|---|
| 20% Ethylene glycol | 0 |
| 0.1M arginine + 20% Ethylene glycol | 0 |
| 0.2M arginine + 20% Ethylene glycol | 0 |
| 0.3M arginine + 20% Ethylene glycol | 0 |
| 0.4M arginine + 20% Ethylene glycol | 1 |
| 0.5M arginine + 20% Ethylene glycol | 10 |
| 0.6M arginine + 20% Ethylene glycol | 37 |

TABLE 3-continued

| Elution conditions* | FVIII found in Eluate, (%) |
|---|---|
| 0.7M arginine + 20% Ethylene glycol | 32 |
| 0.8M arginine + 20% Ethylene glycol | 8 |
| 0.9M arginine + 20% Ethylene glycol | 1 |
| 1.0M arginine + 20% Ethylene glycol | 0 |

*All elution buffers included 0.01M L-Histidine, 0.3M NaCl, 0.01M CaCl$_2$ and 0.02% (w/w) Polysorbate 80, pH 6.5

Conclusion Example 3c (According to the Invention)

As can be seen in table 3, the binding of FVIII to the Capto MMC column can surprisingly be inhibited by a combination of ethylene glycol and arginine. Elution of FVIII is observed in eluates containing up to 0.9M arginine together with 20% (w/w) ethylene glycol.

Example 3d (According to the Invention)

Comparison of Arginine and Lysine as an Elution Component for Capto MMC

Column and Resin
The Capto MMC resin was packed to a bed height of 4-8 cm in a Tricorn 50/100 or C10/20 column (1 column volume (CV)=1.6-3 mL). The Capto MMC resin was obtained from GE Healthcare (Cat. No. 17-5317).
Starting Material
The starting materials used were a protein solution containing rFVIII, obtained as described in example 2.
Equilibration Buffer
0.01 M L-Histidine, 0.01 M CaCl$_2$, 0.3 M NaCl, 0.02% w/w Polysorbate 80, pH 7.0, conductivity 31±3 mS/cm at 25° C.
The column was equilibrated with equilibration buffer followed by loading of the starting material with a flow rate representing a contact time of 1-2 minutes. FVIII bound to the resin during these buffer conditions (no FVIII could be detected in the flow through). The resin was thereafter subjected to different elution conditions as described in Table 4 and the resulting amount of FVIII coming out from the column where analyzed with FVIII:C method and calculated in % in relation to the applied amount of FVIII.

TABLE 4

| Elution conditions* | Eluted volume, (CV) | FVIII found in Eluate, (%) |
|---|---|---|
| 0.5M Lysine + 20% Ethylene glycol | 40 | 3 |
| 0.65M Lysine + 20% Ethylene glycol | 40 | 16 |
| 0.75M Lysine + 20% Ethylene glycol | 40 | 13 |
| 0.4M Arginine + 20% Ethylene glycol | 20 | 4 |
| 0.75M Arginine + 20% Ethylene glycol | 20 | 89 |

*All elution buffers included 0.01M L-Histidine, 0.3M NaCl, 0.01M CaCl$_2$ and 0.02% (w/w) Polysorbate 80, pH 6.5

Conclusion Example 3d (According to the Invention)

As can be seen in table 4, the binding of FVIII to the Capto MMC column has been studied with 20% ethylene glycol in combination with lysine and arginine of different concentration. Arginine elutes FVIII better than lysine, a concentration of 0.75M seems to yield approximately 90% recovery. It seems to be possible to use lower amounts of either amino acid in combination with ethylene glycol, as a wash step to remove impurities from the FVIII molecule, before eluting FVIII with for example 0.75 M arginine.

Example 3e

Evaluation of Purity and Recovery Using Different Wash and Elution Conditions for the Capto MMC Resin Column and Resin The Capto MMC resin was packed in different column sizes (2-9 cm bed height, volume 1.6-48 mL). The Capto MMC resin was obtained from GE Healthcare (Cat. No. 17-5317).

Starting Material

The starting materials used were protein solutions containing rFVIII, obtained as described in example 2, with a typical purity of app. 100 IU FVIII/mg protein (as can be seen in example 9, table 18).

Equilibration Buffer 0.01 M L-Histidine, 0.01 M $CaCl_2$, 0.3 M NaCl, 0.02% w/w Polysorbate 80, pH 7.0, conductivity 31±3 mS/cm at 25° C.

The column was equilibrated with equilibration buffer followed by loading of the starting material with appropriate flow rates (depending on column size, approximately 13-300 cm/h). FVIII bound to the resin during these buffer conditions (no FVIII could be detected in the flow through). The resin was thereafter subjected to different wash and elution conditions as described in Table 5 and the resulting amount of FVIII coming out from the column where analyzed with FVIII:C method and calculated in % in relation to the applied amount of FVIII.

TABLE 5

| Wash buffer | Elution buffer | FVIII recovery, (%) | Purity** eluate, (IU/mg) |
|---|---|---|---|
| 20% ethylene glycol + 0.4M arginine, 40 CV | 0.8M Arginine + 20% ethylene glycol | 83 | 5741 |
| 20% ethylene glycol + 0.45M arginine, 20 CV | 0.8M Arginine | 69 | na |

*All buffers includes 0.01M L-Histidine, 0.3M NaCl, 0.01M $CaCl_2$ and 0.02% (w/w) Polysorbate 80, pH 6.5
**Measured with Bradford Conclusion Example 3e As can be seen in table 5, the combination of 20% ethylene glycol and 0.4M arginine in a wash step before applying higher concentration of arginine in the elution buffer gives high yield and pure product, the concentration of arginine in the wash buffer should not exceed 0.4M due to the relatively low resulting FVIII recovery.

Conclusion Example 3

It becomes clear that the cation multimodal resin (Capto MMC) cannot be eluted using conventional ion-exchanger elution conditions (high salt) or hydrophobic interaction resins (low salt). An increased amount of charged amino acid alone or in combination with ethylene glycol could surprisingly release the bound FVIII molecule from the Capto MMC resin. In addition, NaCl, arginine, lysine and ethylene glycol concentrations could be varied during wash and elution of the resin, to optimize recovery and purity of the Capto MMC eluate.

Example 4

Elution Conditions for Multimodal Anion Resin Capto Adhere (Comparative)

The following series of experiments where performed to evaluate different elution conditions on the multimodal anion resin Capto Adhere.

Column and Resin

The Capto Adhere resin was packed to a bed height of 13.5 cm in a C10/20 column. The Capto Adhere resin was obtained from GE Healthcare (Cat. No. 17-5444).

Starting Material

The starting materials used were a protein solution containing rFVIII, obtained as described in example 6C.

Equilibration Buffer 0.01 M L-Histidine, 0.01 M $CaCl_2$, 0.3 M NaCl, 0.02% w/w Polysorbate 80, pH 6.5, conductivity 30±3 mS/cm at 25° C.

The column was equilibrated with equilibration buffer followed by loading of the starting material. The resin was thereafter subjected to different elution conditions as described in Table 6 and the resulting amount of FVIII coming out from the column was analyzed.

TABLE 6

| Sample | Volume, ml | FVIII, IU/ml | Total FVIII, IU | Total FVIII, (%) |
|---|---|---|---|---|
| Starting material (load) | 184 | 140 | 25760 | 100 |
| A (Equilibration buff.) | 159 | 0.0 | 0 | 0 |
| B (High salt) | 212 | 0.0 | 0 | 0 |
| C (Low salt) | 53 | 0.0 | 0 | 0 |
| D (Low Aminoacid + Low Ethylene Glycol) | 212 | 3.5 | 935 | 4 |
| E (Aminoacid) | 32 | 701 | 22432 | 87 |

Elution Condition A 0.01 M L-Histidine, 0.01 M $CaCl_2$, 0.3 M NaCl, 0.02% w/w Polysorbate 80, pH 6.5, conductivity 30±3 mS/cm at 25° C.

Elution Condition B (High Salt)

0.05 M L-Histidine, 0.05 M $CaCl_2$, 2.0 M NaCl, 0.02% w/w Polysorbate 80, pH 6.5, conductivity 140±5 mS/cm at 25° C.

Elution Condition C (Low Salt)

0.01 M L-Histidine, 0.01 M $CaCl_2$, 0.1 M NaCl, 0.02% w/w Polysorbate 80, pH 6.5, conductivity 13±3 mS/cm at 25° C.

Elution Condition D (Low Amino Acid+Low Ethylene Glycol)

0.01 M L-Histidine, 0.01 M $CaCl_2$, 0.3 M NaCl, 0.3M Arginine hydrochloride, 20% w/w ethylene glycol, 0.02% w/w Polysorbate 80, pH 6.5, conductivity 28±3 mS/cm at 25° C.

Elution Condition E (Amino Acid)

0.01 M L-Histidine, 0.01 M $CaCl_2$, 0.3 M NaCl, 0.8M Arginine hydrochloride, 0.02% w/w Polysorbate 80, pH 6.5, conductivity 53±2 mS/cm at 25° C.

Conclusion Example 4

It becomes clear that the anion multimodal resin (Capto Adhere) cannot be eluted using convention ion-exchanger elution conditions (high salt) or hydrophobic interaction resins (low salt). An increased amount of a charged aminoacid alone or in combination with ethylene glycol could surprisingly release the bound FVIII molecule.

Example 5

Comparison of a Conventional Cation Exchange Step (SP Sepharose FF) with a Cation Multimodal Resin (Capto MMC) as a Purification Step (Capture Step)

Column and Resin

The Capto MMC resin was packed to a bed height of 11 cm in a C10/20 column (1 column volume (CV)=8.5 mL). The Capto MMC resin was obtained from GE Healthcare (Cat. No. 17-5317).

The SP Sepharose FF resin was packed to a bed height of 18 cm in a XK26/20 column (1 column volume (CV)=100 mL). The SP Sepharose FF resin was obtained from GE Healthcare (Cat. No. 17-0729).

Starting Material

The starting materials used were a protein solution containing rFVIII, obtained as described in example 2 (identical start material was used for both experiments). For the SP Sepharose FF resin, the starting material was diluted with dilution buffer to a conductivity of 12 mS before applying to the resin, for FVIII to be able to bind.

Dilution Buffer SP 0.01 M L-Histidine, 0.01 M $CaCl_2$, 0.07 M NaCl, 0.02% w/w Polysorbate 80, pH 6.5

Equilibration Buffer MMC 0.01 M L-Histidine, 0.01 M $CaCl_2$, 0.3 M NaCl, 0.02% w/w Polysorbate 80, pH 7.0, conductivity 31±3 mS/cm at 25° C.

Equilibration Buffer SP 0.01 M L-Histidine, 0.01 M $CaCl_2$, 0.1 M NaCl, 0.02% w/w Polysorbate 80, pH 6.5, conductivity 12±2 mS/cm at 25° C.

The columns was equilibrated with equilibration buffer followed by loading of the starting material at a flow rate of 5 mL/min respectively 40 mL/min. FVIII bound to the resins during these buffer conditions (no FVIII could be detected in the flow through). The resin was thereafter subjected to different wash and elution conditions, the principle described in example 3d (wash 0.75M lysine+20% ethylene glycol) and example 3b (elution 1.5M NaCl+50% ethylene glycol) for the Capto MMC step and in example 6b for the SP Sepharose FF step (wash 0.15M NaCl and elution 0.36M NaCl). In Table 7 the differences between the two purification steps can be studied.

Conclusion Example 5 (Comparative)

The result of table 7 show, that the use of the Capto MMC step as a capture/purification step for FVIII exerts several advantages including:
Better FVIII recovery
Higher purity in regard of host cell proteins
Higher purity in regard of DNA
Higher binding capacity FVIII/mL resin
Shorter process time due to less dilution (the MMC resin can be processed with a higher conductivity)

Example 6

Specific Elution (Ca) and Wash Components for FVIII and Purification Thereof on a Cation Exchange Resin (SP Sepharose FF) (Comparative)

The following series of experiments where performed to evaluate different elution conditions on the SP Sepharose FF resin.

Example 6a

Sodium Chloride and Arginine as Specific Elution and Wash Component Used on a Cation Exchange Resin (SP Sepharose FF)

Column and Resin

The SP Sepharose FF resin was packed to a bed height of 15 cm in a XK16 column. The SP Sepharose FF resin was obtained from GE Healthcare (Cat. No. 17-0729).

Starting Material

The starting materials used were a protein solution containing rFVIII, obtained as described in example 2 and further processed on a Capto MMC resin, as described in example 9. The eluate from the Capto MMC column was diluted 12× with a dilution buffer to lower the conductivity to approximately 12 mS/cm, which enables the binding of the target protein to the SP Sepharose FF resin.

Dilution Buffer 0.01 M L-Histidine, 0.01 M $CaCl_2$, 0.07 M NaCl, 0.02% w/w Polysorbate 80, pH 6.5

Equilibration Buffer 0.01 M L-Histidine, 0.01 M $CaCl_2$, 0.1 M NaCl, 0.02% w/w Polysorbate 80, pH 6.5, conductivity 12±2 mS/cm at 25° C.

The column was equilibrated with equilibration buffer followed by loading of the starting material. The resin was thereafter subjected to different elution conditions as described in Table 8 and the resulting amount of FVIII leaving the column was analyzed.

TABLE 7

| Capture Resin | Conductivity in loading material, mS/cm at 25° C. | Volume Loading material, mL | Total applied FVIII, IU | FVIII/mL Capture resin | FVIII recovery*, % | Purity**, IU/mg | DNA/ FVIII, ng/IU |
|---|---|---|---|---|---|---|---|
| Capto MMC OgH07-648 | 35 | 1235 | 29022 | 3400 | 68% | 2414 | 2.3 |
| SP-Seph FF OgH07-647 | 12 | 5759 | 20147 | 202 | 59% | 596 | 22.1 |

*Calculated from undiluted starting material
**Measured with Bradford

TABLE 8

| Sample | Volume ml | FVIII IU/ml | Total FVIII, IU | Total % | Specific Activity** IU/mg |
|---|---|---|---|---|---|
| Starting material (load) | 2830 | 5 | 14150 | 100 | 178 |
| Equilibration buff. Wash | 300 | 0.0 | 0 | 0 | na |
| Wash A | 600 | 0.0 | 0 | 0 | na |
| Elution | 90 | 153 | 13770 | 97 | 362 | na—Not analyzed
**Measured with Bradford

Wash A
0.01 M L-Histidine, 0.01 M $CaCl_2$, 0.15 M NaCl, 0.02% w/w Polysorbate 80, pH 6.5, conductivity 16.5-18.0 mS/cm at 25° C.

Elution Buffer
0.01 M L-Histidine, 0.035 M $CaCl_2$, 0.34 M NaCl, 0.2M D-sorbitol, 0.045M arginine hydrochloride, 0.02% w/w Polysorbate 80, pH 6.5, conductivity 36±2 mS/cm at 25° C.

Conclusion Example 6a (Comparative)

The bound FVIII was effectively eluted from the SP Sepharose FF column when an eluting buffer with a conductivity of 36 mS/cm was used. This conductivity was an effect of the NaCl concentration and partly of the $CaCl_2$ and arginine concentrations. The sorbitol and arginine was included in the buffer to stabilize the FVIII molecule during processing, freezing and thawing.

Example 6b

Sodium Chloride as a Specific Elution and Wash Component Used on a Cation Exchange Resin (SP Sepharose FF)

Column and Resin
The SP Sepharose FF resin was packed to a bed height of 15 cm in a C10/20 column. The SP Sepharose FF resin was obtained from GE Healthcare (Cat. No. 17-0729).

Starting Material
The starting materials used were a protein solution containing rFVIII, obtained as described in example 2 and example 9. The eluate from the Capto MMC column was diluted 12× with a dilution buffer to lower the conductivity, which enables the binding of the target protein to the SP Sepharose FF resin.

Dilution Buffer
0.01 M-Histidine, 0.01 M $CaCl_2$, 0.01 M NaCl, 0.02% w/w Polysorbate 80, pH 6.5

Equilibration Buffer
0.01 M-Histidine, 0.01 M $CaCl_2$, 0.1 M NaCl, 0.02% w/w Polysorbate 80, pH 6.5, conductivity 12±2 mS/cm at 25° C.

The column was equilibrated with equilibration buffer followed by loading of the starting material. The resin was thereafter subjected to different elution conditions as described in Table 9 and the resulting amount of FVIII leaving the column was analyzed.

TABLE 9

| Sample | Volume ml | FVIII IU/ml | Total FVIII, IU | Total FVIII, % | Specific Activity** IU/mg |
|---|---|---|---|---|---|
| Starting material (load) | 540 | 12.8 | 6912 | 100 | 799 |
| Wash Equilibration buffer | 120 | 0.0 | 0 | 0 | na |
| Wash B | 490 | 0.0 | 0 | 0 | na |
| Elution | 27 | 221 | 5967 | 86 | 948 |

**Measured with Bradford

Wash B
0.01 M L-Histidine, 0.01 M $CaCl_2$, 0.15 M NaCl, 0.02% w/w Polysorbate 80, pH 6.5, conductivity 16.5-18.0 mS/cm at 25° C.

Elution Buffer
0.01 M L-Histidine, 0.035 M $CaCl_2$, 0.36 M NaCl, 0.2M D-Sorbitol, 0.02% w/w Polysorbate 80, pH 6.5, conductivity 36±2 mS/cm at 25° C.

Conclusion Example 6B

An eluting buffer with a conductivity of 36 mS/cm was used. Compared to the one used in experiment 5a the arginine was excluded and the conductivity was adjusted to 36 mS/cm by adding a slightly higher NaCl concentration. The percent eluted FVIII was slightly lower than in experiment 5a indicating that arginine has a positive function during the process.

Example 6

Calcium Chloride as a Specific Elution and Wash Component Used on a Cation Exchange Resin Column and Resin
The SP Sepharose FF resin was packed to a bed height of 15.5 cm in a XK26 column. The SP Sepharose FF resin was obtained from GE Healthcare (Cat. No. 17-0729).

Starting Material
The starting materials used were a protein solution containing rFVIII, obtained as described in example 2 and example 9. The eluate from the Capto MMC column was diluted 12× with a dilution buffer to lower the conductivity, which enables the binding of the target protein to the SP Sepharose FF resin.

Dilution Buffer
0.01 M L-Histidine, 0.01 M $CaCl_2$, 0.05 M NaCl, 0.02% w/w Polysorbate 80, pH 6.5

Equilibration Buffer
0.01 M L-Histidine, 0.01 M $CaCl_2$, 0.1 M NaCl, 0.02% w/w Polysorbate 80, pH 6.5, conductivity 12±2 mS/cm at 25° C.

The column was equilibrated with equilibration buffer followed by loading of the starting material. The resin was thereafter subjected to different elution conditions as described in Table 10 and the resulting amount of FVIII leaving the column was analyzed.

TABLE 10

| Sample | Volume ml | FVIII IU/ml | Total FVIII, IU | Total FVIII, % | Specific Activity** IU/mg |
|---|---|---|---|---|---|
| Starting material (load) | 2000 | 31.7 | 63400 | 10 | 578 |
| Wash Equilibration buffer | 830 | 0.0 | 0 | 0 | na |

TABLE 10-continued

| Sample | Volume ml | FVIII IU/ml | Total FVIII, IU | Total FVIII, % | Specific Activity** IU/mg |
|---|---|---|---|---|---|
| Wash B | 3320 | 0.0 | 0 | 0 | na |
| Wash C (Sorbitol) | 249 | 0 | 0 | 0 | na |
| Elution (Calcium chloride) | 410 | 149 | 61090 | 96 | 2811 |

**Measured with Bradford

Wash B 0.01 M L-Histidine, 0.01 M $CaCl_2$, 0.15 M NaCl, 0.02% w/w Polysorbate 80, pH 6.5, conductivity 16.5-18.0 mS/cm at 25° C.

Wash C (Sorbitol) 0.01 M L-Histidine, 0.01 M $CaCl_2$, 0.1 M NaCl, 0.2M D-Sorbitol, 0.02% w/w Polysorbate 80, pH 6.5, conductivity 12±2 mS/cm at 25° C.

Elution Buffer (Calcium Chloride)

0.02 M L-Histidine, 0.2 M $CaCl_2$, 0.1 M NaCl, 0.2M D-sorbitol, 0.02% w/w Polysorbate 80, pH 6.5, conductivity 18.7 (18.0-19.0) mS/cm at 25° C.

Conclusion Example 6c (6a, 6b)

In this experiment (6c) the NaCl concentration was lowered and a higher $CaCl_2$ concentration was used, in the elution buffer. This change resulted in a conductivity of 18.7 mS/cm. The eluting capacity of the FVIII from the SP Sepharose FF was equally good as in experiment 5a were the conductivity in the elution buffer was 36 mS/cm. It was an unexpected finding that the FVIII recovery was equal or better with an elution buffer with almost half of the conductivity. In ion exchange chromatography, normally, the elution of proteins is strongly dependent on the conductivity (ionic strength) or/and the pH. In this example it seems that the $Ca^{2+}$ ion exerts specific effects, other than solely from the ionic strength, on the FVIII molecule. This is also verified by the purity, which is higher (2811 compared with 362 and 948 respectively in 6a and 6b) when using the Ca-based elution with lower conductivity.

Example 7

Purification with a Yeast Derived FVIII Affinity Ligand

The following experiment was performed to evaluate the elution conditions on the affinity resin VIIISelect.

Column and Resin

A C10/20 column was packed with the VIIISelect resin to a bed height of seven cm. The VIIISelect resin was obtained from GE Healthcare (Cat. No. 17-5450).

Starting Material

The starting material used was a SP Sepharose eluate containing rFVIII, obtained as principle described in example 6b for the SP Sepharose FF step (wash 0.15M NaCl and elution 0.36M NaCl).

Buffer Compositions:

Buffer A (Equilibration buffer with S/D chemicals added)

0.3 mol/kg NaCl, 0.02 mol/kg $CaCl_2$ ($2 \times H_2O$), 0.02 mol/kg L-Histidine, 1% w/w Triton X-100, 0.3% w/w TNBP, pH: 6.5±0.1, Conductivity: 31±3 mS/cm at +25° C.

Wash B (Equilibration Buffer without S/D Chemicals)

0.3 mol/kg NaCl, 0.02 mol/kg $CaCl_2$, 0.02 mol/kg L-Histidine, 0.02% (w/w) Polysorbate 80, pH: 6.5±0.1, Conductivity: 31±3 mS/cm at +25° C.

Wash C (High Salt Concentration Wash Buffer)

1.0 mol/kg NaCl, 0.02 mol/kg $CaCl_2$, 0.02 mol/kg L-Histidine, 0.02% (w/w) Polysorbate 80, pH: 6.5±0.1, Conductivity: 85±3 mS/cm at +25° C.

Buffer D (Elution Buffer)

1.5 mol/kg NaCl, 0.02 mol/kg $CaCl_2$, 0.02 mol/kg L-Histidine, 0.02% (w/w) Polysorbate 80, 50% (w/w) ethylene glycol (EG), pH: 6.5±0.1, Conductivity: 39±3 mS/cm at +25° C.

The equilibration, washing and elution buffers are not limited to the stated pH, concentrations, and type of buffer, salts or detergent.

The column was equilibrated with equilibration buffer A followed by loading of the starting material. The resin was thereafter subjected to different wash and elution conditions as described in Table 11 and the resulting amount of FVIII leaving the column where analyzed.

TABLE 11

Results from VIIISelect experiment

| Sample | Volume (ml) | FVIII (IU/ml) | Total (IU) | Total (%) | Specific Activity (IU/mg protein) | DNA content (pg/1000 IU) |
|---|---|---|---|---|---|---|
| Starting material (load) | 45 | 483 | 21735 | 100 | 1959* | 1681 |
| Wash B, | 127.5 | 0.1 | 13 | 0 | — | — |
| Wash C | 55 | 0 | 0 | 0 | — | — |
| Elution | 27.5 | 642 | 17655 | 81 | 8758* | 1399 |

*Measured with Bradford

FIG. 1 Silver stained SDS-PAGE showing purity profile for starting material (Lane 1) and VIIISelect eluate (Lane 2) after the affinity chromatography step.

Conclusion Example 7

The VIIISelect step is a powerful purification step that yields a pure eluate.

Example 8

Comparison of a Purification Sequence with VIIISelect Affinity Resin or a Multi Modal Resin (Capto Adhere) Instead (Appendix 3)

The two different purification schemes were performed in small scale according to example 7 (VIIISelect) and example 10 (Capto Adhere)

TABLE 12

Comparison of FVIII recovery and purity by use of FVIIISelect or Capto Adhere purification step

| VIIISelect Scheme | Specific activity (IU/mg total protein) | FVIII, IU Recovery (%) | DNA Content (pg/1000IU) | Capto Adhere scheme | Specific activity (IU/mg total protein) | FVIII, IU Recovery (%) | DNA content (pg/1000 IU) |
|---|---|---|---|---|---|---|---|
| Starting material (Sp-filtrate) | 1588* | 100 | 1442 | Starting material (Sp-filtrate) | 1588* | 100 | 1442 |
| VIIISelect eluate | 8759* | 81 | 1399 | Adhere eluate | 5112* | 86 | 504 |
| Q-eluate VIIISelect | na | 106 | 840 | Q-eluate (Adhere) | na | 105 | 82 |
| GF-eluate VIIISelect | 10322 | 88 | 214 | GF-eluate (Adhere) | 10679 | 103 | 181 | n.a. = Not analyzed
*Measured with Bradford
**Measured with amino acid analysis

Figure 2:
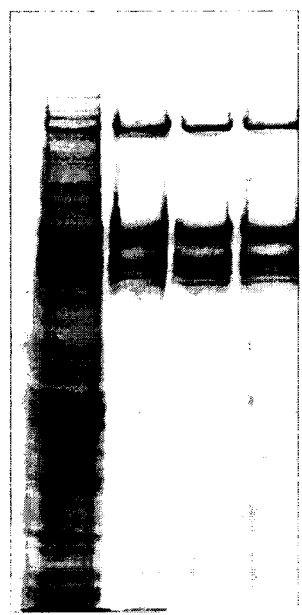
Figure 2:
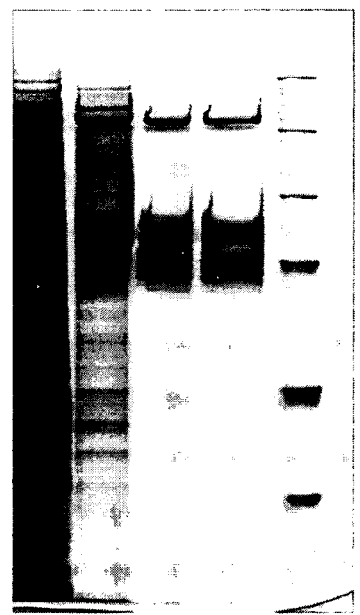

FIG. 2 shows SDS Page silver staining of samples described in Table 12; Comparison of VIIISelect purification scheme and Capto Adhere purification scheme.

Lane 1 shows the purity of the starting material (SP-filtrate) before the VIIISelect column loaded at a FVIII concentration of 483 IU/ml.

Lane 2 shows the purity of the VIIISelect eluate loaded at a FVIII concentration of 500 IU/ml.

Lane 3 shows the purity after the purification sequence SP-VIIISelect-Q Seph, loaded at a FVIII concentration of 500 IU/ml.

Lane 4 shows the purity after the purification sequence SP-VIIISelect-Q Seph-gelfiltration, loaded at a FVIII concentration of 385 IU/ml.

Lane 5 shows the purity of the starting material (SP-filtrate) before the Capto Adhere column loaded at a FVIII concentration of 493 IU/ml.

Lane 6 shows the purity of the Capto adhere eluate loaded at a FVIII concentration of 500 IU/ml.

Lane 7 shows the purity after the purification sequence SP-Capto Adhere-Q Seph, loaded at a FVIII concentration of 500 IU/ml.

Lane 8 shows the purity after the purification sequence SP-Capto Adhere-Q Seph-gelfiltration, loaded at a FVIII concentration of 493 IU/ml.

Lane 9 shows a molecular marker

Conclusion Example 8

The same purity can be achieved either by using the VIIISelect affinity step or the Capto Adhere chromatography step, if the purity is compared in the final product (GF-eluate). The purity after the VIIISelect step is higher compared to after the Capto Adhere step, but after the remaining purification steps (Q and GF) no difference in purity can be noticed with used analytical methods. The recovery using the Capto Adhere step is slightly higher compared to the sequence using VIIISelect.

Example 9

Industrial Scale Purification Sequence, Including Viiiselect Affinity Resin

To study the reproducibility of recovery and purity, purification Steps 1-9 described below, were performed on 3-4 batches in pilot scale. Each batch originating from 40-100 L cell suspension, as described in example 1-2.

Step 1 DNA Reduction Step No. 1 (Anion Chromatography)

Primary reduction of DNA is done with filtration through a Q-membrane (Sartobind Q, Sartorious). The Q-membrane is equilibrated with buffer prior to filtration (Table 13).

TABLE 13

| Buffer used for Q-Membrane | | |
|---|---|---|
| Q-Membrane/ DNA-reduction | Equilibration buffer | 0.3 mol/kg NaCl, 0.01 mol/kg CaCl$_2$, 0.01 mol/kg L-histidine, 0.02% Polysorbate 80, pH 7 |

The cellfiltrate (from example 2) is processed through the Q-membrane and the product-containing flow-through is collected. The membrane is washed with equilibration buffer to recover any FVIII remaining in the membrane.

Step 2 Capture Step (Multi Modal Chromatography, Capto Mmc)

The primary product purification and concentration (capture) is performed at 500-10,000 IU of FVIII/ml of multimodal cation exchange chromatography (Capto MMC) gel. The gel is before product application equilibrated with Capto MMC equilibration buffer. The filtrate from step 1 is loaded to the Capto MMC column which thereafter is rinsed with Capto MMC equilibration buffer and thereafter washed sequentially with wash buffer 1-3 followed by elution of FVIII, as described in Table 14.

TABLE 14

| Multi Modal Chromatography/ Capto MMC | Equilibration buffer | 0.3 mol/kg NaCl, 0.01 mol/kg $CaCl_2$, 0.01 mol/kg L-histidine, 0.02% Polysorbate 80 (w/w), pH 7 |
|---|---|---|
| | Wash Buffer 1 | 1 mol/kg NaCl, 0.05 mol/kg $CaCl_2$, 0.05 mol/kg L-histidine, 0.02% (w/w) Polysorbate 80, pH 6.5 |
| | Wash Buffer 2 | 0.1 mol/kg NaCl, 0.01 mol/kg $CaCl_2$, 0.01 mol/kg L-histidine, 0.02% (w/w) Polysorbate 80, pH 6.5. |
| | Wash Buffer 3 | 0.3 mol/kg NaCl, 0.01 mol/kg $CaCl_2$, 0.01 mol/kg L-histidine, 0.4 mol/kg L-arginine hydrochloride, 10% (w/w) ethylene glycol, 0.02% Polysorbate 80 (w/w), pH 6.5 |
| | Elution Buffer | 0.3 mol/kg NaCl, 0.02 mol/kg $CaCl_2$, 0.02 mol/kg L-histidine, 0.8 mol/kg L-arginine hydrochloride 10% (w/w) ethylene glycol, 0.02% Polysorbate 80 (w/w), pH 6.5 |

Step 3 Cation Exchange Chromatography, SP Sepharose FF

The FVIII-containing solution (Capto MMC eluate) from step 2 is further purified using a SP-Sepharose FF gel (GE Healthcare Cat. No. 17-0729). Before product application the column is equilibrated with SP-Sepharose equilibration buffer and the protein solution is diluted to meet the ionic strength and pH of the equilibration buffer, to be able to bind FVIII to the gel. The diluted protein solution is applied to the SP Sepharose column, which thereafter is rinsed with equilibration buffer and thereafter washed with wash buffer followed by elution of FVIII, as described in Table 15.

TABLE 15

Buffers used for Cation Exchange Chromatography

| Cation exchange Chromatography (SP Sepharose FF) | Equilibration Buffer | 0.1 mol/kg NaCl, 0.01 mol/kg, L-histidine, 0.01 mol/kg $CaCl_2$, 0.02% Polysorbate 80 (w/w), pH 6.5 |
|---|---|---|
| | Wash Buffer | 0.15 mol/kg NaCl, 0.01 mol/kg, L-histidine, 0.01 mol/kg $CaCl_2$, 0.02% Polysorbate 80 (w/w), pH 6.5 |
| | Elution Buffer | 0.34 mol/kg NaCl, 0.035 mol/kg $CaCl_2$, 0.045 mol/kg L-arginine hydrochloride, 0.2 mol/kg Sorbitol, 0.01 mol/kg L-histidine, 0.02% Polysorbate 80 (w/w), pH 6.5 |

Step 4 DNA Reduction Step No. 2 (Anion Chromatography)

Secondary reduction of DNA is done with filtration through a Q-membrane (Sartobind Q, Sartorious). The Q-membrane is equilibrated with buffer prior to filtration (Table 16).

TABLE 16

Buffer used for Q-Membrane

| Q-Membrane/ DNA-reduction | Equilibration buffer | 0.34 mol/kg NaCl, 0.035 mol/kg $CaCl_2$, 0.045 mol/kg L-arginine hydrochloride, 0.2 mol/kg Sorbitol, 0.01 mol/kg L-histidine, 0.02% Polysorbate 80 (w/w), pH 6.5 |
|---|---|---|

The SP-eluate from step 3 is filtered through the Q-membrane, the product-containing flow-through is collected for further processing. The membrane is washed with equilibration buffer to recover any FVIII remaining in the membrane.

Step 5 Virus Inactivation (Solvent/Detergent (S/D) Treatment)

The filtrate from step 4 is virus inactivated through S/D (Solvent/Detergent) treatment with 1% Triton X-100 and 0.3% Tri-(N-Butyl)-Phosphate (TNBP). Virus inactivation is performed under agitation at room temperature for approximately 1 h.

Step 6 Purification with a Yeast Derived Affinity Chromatography Resin

The virus inactivated FVIII solution from step 5 is processed through a VIIISelect affinity column according to description in example 7. Approximately 5-20,000 IU FVIII is loaded per mL resin.

Step 7 Nanofiltration

The VIIISelect eluate from step 6 is nanofiltered for removal of potential adventitious agents such as non-enveloped viruses, using a Planova 20N nanofilter (Asahi Kasei Medical). The product containing flow through is collected.

Step 8 Anion Exchange Chromatography Step (Q-Sepharose FF)

The Q Sepharose FF resin was obtained from GE Healthcare (Cat. No. 17-0510). The starting material used is a nanofiltrate obtained from step 7, whereas the salt and pH has been adjusted to be comparable to the equilibration buffer in Table 17. The diluted protein solution is applied to the Q Sepharose FF column with a load of 5,000-25,000 IU/mL gel, which thereafter is rinsed with equilibration buffer and thereafter washed with wash buffer followed by elution of FVIII, as described in Table 17.

TABLE 17

| Buffer used for anion exchange step (Q-Sepharose FF) | | |
| --- | --- | --- |
| Anion exchanger/ Q-Sepharose FF | Equilibration Buffer | 0.1 mol/kg NaCl, 0.02 mol/kg $CaCl_2$, 0.02 mol/kg L-histidine, 0.02% Polysorbate 80, pH 7.5 |
| | Wash Buffer | 0.3 mol/kg NaCl, 0.02 mol/kg $CaCl_2$, 0.02 mol/kg L-histidine, 0.02% Polysorbate 80 pH 7.5 |
| | Elution Buffer | 0.4 mol/kg NaCl, 0.02 mol/kg $CaCl_2$, 0.02 mol/kg L-histidine, 0.02% Polysorbate 80 pH 6.0 |

Step 9 Gel Filtration Chromatography Step

A gelfiltration resin (Superdex 200 pg, GE Healthcare Cat. No. 17-1043) was packed to a bed height of 60-75 cm. The starting material used is the Q-eluate obtained from step 8. The column is equilibrated with a physiological acceptable composition which protect the product from surface adsorption and stabilize it during freezing, storage, freeze drying etc. The Q-eluate is applied to the gelfiltration column with a volume of 2-8% of the total column volume. The formulated FVIII containing eluate, devoid of fragment and aggregates, is collected after the column (GF-eluate).

TABLE 18

Summary of results over the purification steps described in step 1-4, of four pilot scale purification batches (originating from approximately 50 L (BPP077-078) and 100 L (BPP080-081) cell suspension material (described in example 1).

| | BPP077 | BPP078 | BPP080 | BPP081 |
| --- | --- | --- | --- | --- |
| Starting material (described in example 2) | | | | |
| Weight (kg) | 81 | 72 | 162 | 160 |
| Total FVIII (IU) | 2327570 | 1699200 | 4032180 | 3870400 |
| FVIII yield (%) | 100 | 100 | 100 | 100 |
| Specific activity* (IU/mg) | 83 | 67 | 107 | 107 |
| DNA content (pg/1000 IU) | $1.4*10^8$ | $5.93*10^9$ | $5.3*10^9$ | — |
| MMC-eluate (step 2) | | | | |
| Weight (kg) | 3.5 | 4.4 | 10.9 | 9.6 |
| Total FVIII (IU) | 412654 | 1023103 | 3844487 | 3428212 |
| FVIII yield (%) | 24 | 70 | 104 | 96 |
| Specific activity* (IU/mg) | 846 | 512 | 578 | 646 |
| DNA content (pg/1000 IU) | $1.8*10^5$ | $1.1*10^6$ | $4.6*10^6$ | — |
| SP-filtrate (step 4) | | | | |
| Weight (kg) | 3.1 | 3.3 | 5.0 | 4.6 |
| Total (IU) | 1524582 | 1025994 | 3430796 | 3000515 |
| FVIII (%) | 112 | 116 | 119 | 108 |
| Specific activity* (IU/mg) | 1588 | 793 | 1362 | 1277 |
| DNA content (pg/1000 IU) | <206 | 4463 | 1313 | — |

*Measured with Bradford
Capture harvest batches BPP077 and BPP078 where pooled to downstream purification batch BPP079, whereas batch BPP080 was denoted BPP083 and BPP081 denoted BPP084.

TABLE 19

Summary of results over the chromatography steps described in step 5-9, in the downstream part of three pilot scale purification batches

| | BPP079 | BPP083 | BPP084 |
| --- | --- | --- | --- |
| Starting material (step 4) | | | |
| Weight (kg) | 5476 | 4928 | 4220 |
| Total FVIII, (IU) | 1642680 | 2389094 | 2022646 |
| FVIII yield, (%) | 100 | 100 | 100 |

TABLE 19-continued

Summary of results over the chromatography steps described in step 5-9, in the downstream part of three pilot scale purification batches

|  | BPP079 | BPP083 | BPP084 |
|---|---|---|---|
| Specific activity*** (IU/mg) | 1107 | 1254 | 1210 |
| DNA content (pg/1000 IU) | 3733 | — | — |
| VIIISelect-eluate (step 6) | | | |
| Weight (g) | 666 | 785 | 810 |
| Total FVIII (IU) | 1251414 | 2094380 | 1674270 |
| FVIII yield (%) | 76 | 88 | 83 |
| Specific activity*** (IU/mg) | 8064 | — | — |
| DNA content (pg/1000 IU) | 1554 | — | — |
| Nanofiltrate (step 7) | | | |
| Weight (g) | 7680 | 8205 | 9555 |
| TotalFVIII, (IU) | 1051392 | 1822331 | 1763853 |
| FVIII yield (%) | 94 | 88 | 97 |
| Specific activity (IU/mg) | — | — | — |
| DNA content (pg/1000 IU) | <730 | — | — |
| Q-eluate (step 8) | | | |
| Weight (kg) | 281 | 291 | 263 |
| Total FVIII (IU) | 1002327 | 1755603 | 1857832 |
| FVIII yield* (%) | 95 | 96 | 105 |
| Specific activity**** (IU/mg) | 10975 | — | 10312 |
| DNA content (pg/1000 IU) | 47 | 43 | <14 |
| GF-eluate (step 9) | | | |
| Weight (kg) | 562 | 740 | 860 |
| Total FVIII (IU) | 627754 | 1124800 | 926220 |
| FVIII yield** (%) | 79 | 116 | 101 |
| Specific activity**** (IU/mg) | 12275 | 10000 | 10663 |
| DNA content (pg/1000 IU) | — | <66 | — |

Figure 3:
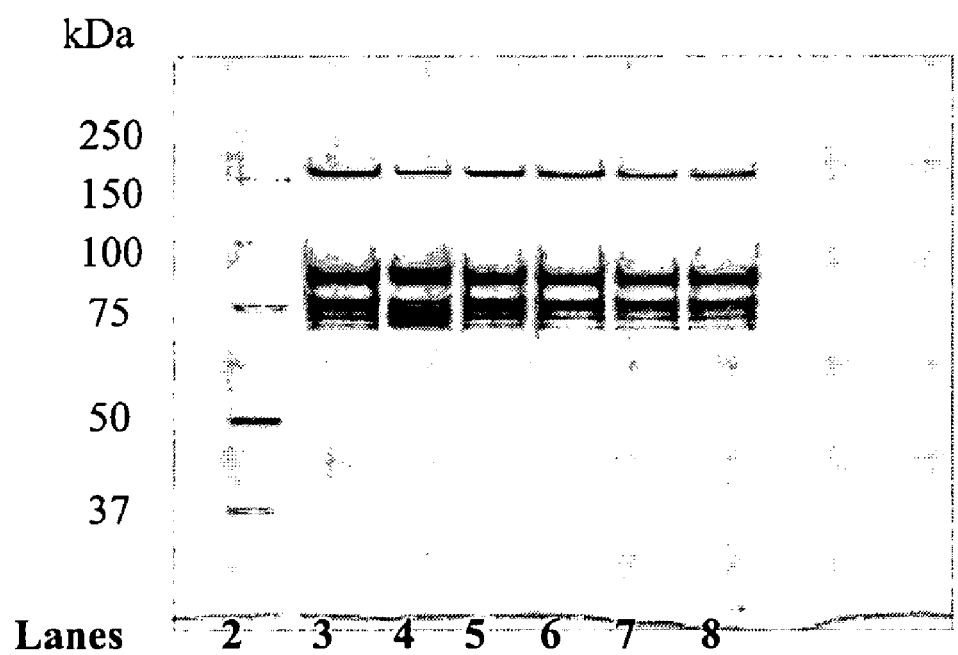

*Yield calculated over the Q step,
**Yield calculated over the GF step,
***Measured with Bradford
****Measured with Amino acid analysis FIG. 3 shows SDS-PAGE silver staining pattern of the final product before (Lane 3—BPP083, Lane 7—BPP084) and after (Lane 6—C810A139, Lane 8—C811A139) formulation, purified according to example 9 (Table 18-19). Lane 2 shows a molecular marker, Lane 3 shows a FVIII control sample and Lane 4 shows a commercially available FVIII product (ReFacto®—Lot C66202).

Figure 4:
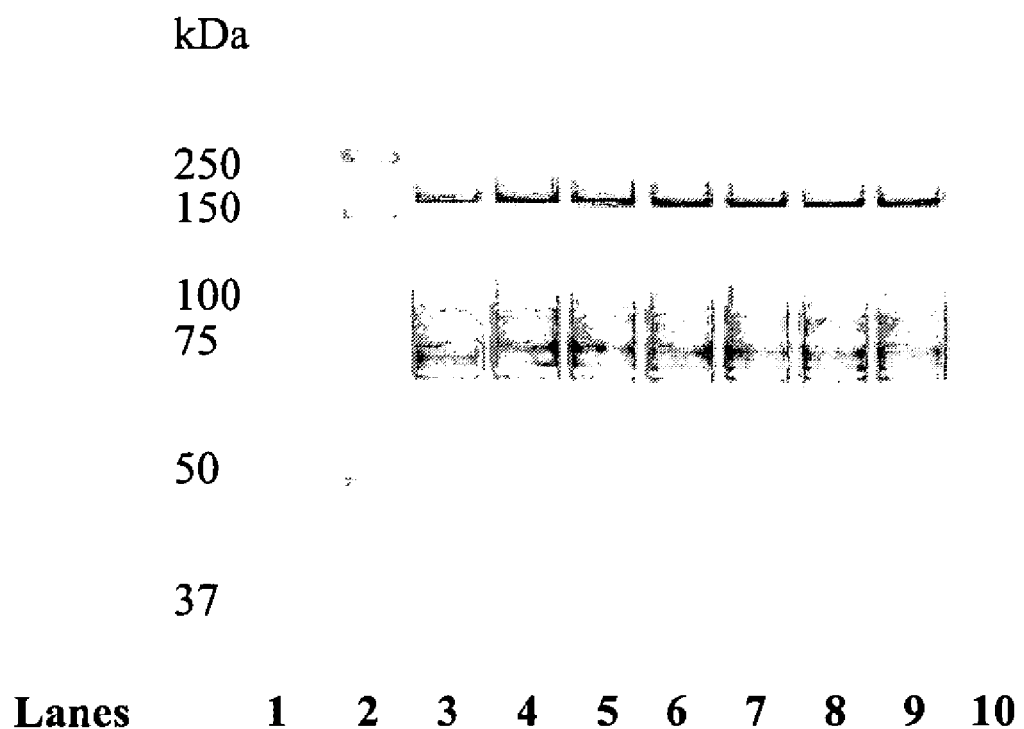

FIG. 4 shows Western blotting of FVIII using polyclonal anti-human FVIII antibodies. Lanes 1 and 10 are Empty, Lane 2 shows a Molecular mass standard (Precision Plus Protein Western C from Bio-rad), Lane 3 shows a commercially available FVIII product ReFacto® lot C66202, Lane 4-6, shows a FVIII control samples, Lanes 7-9 shows final formulated products of batches BPP079, BPP083 and BPP084 purified according to example 9 (Table 17-18). Samples were diluted to a FVIII concentration corresponding to 5 IU FVIII:C/ml before applying to the western blot.

Figure 5A:
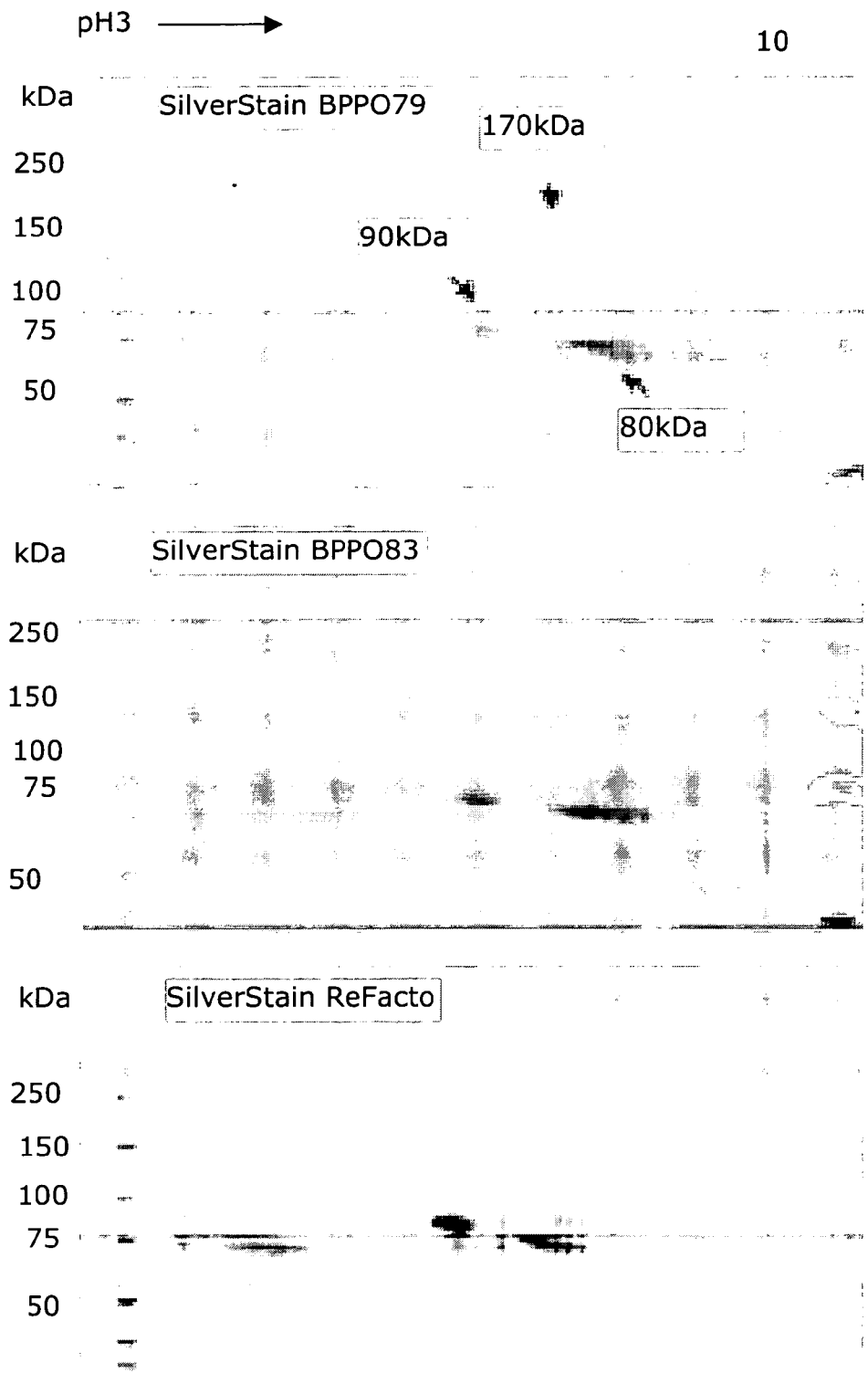
Figure 5B:
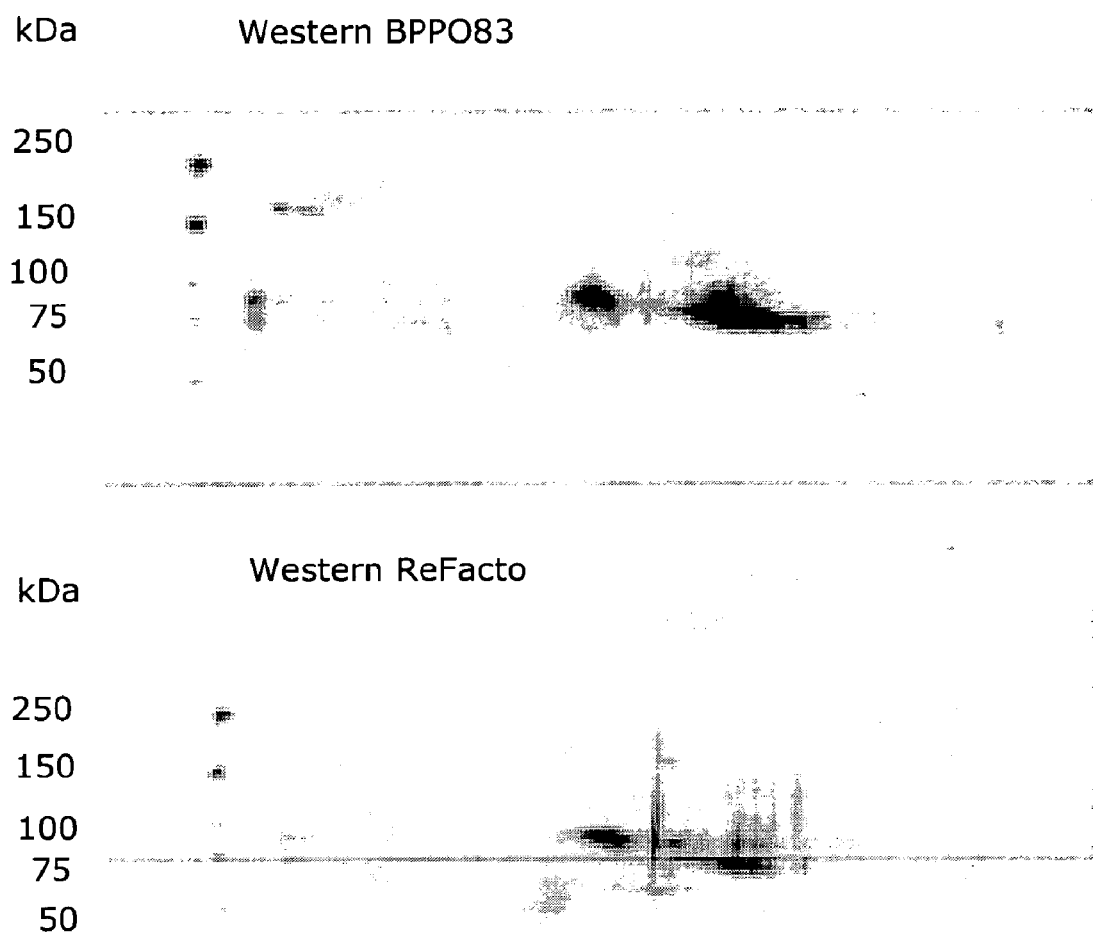

FIG. 5 shows 2-D-PAGE following silver-staining and western blotting of final formulated products of batches BPP079 and BPP083, final product (GF-eluate) of batches BPP079 GF eluate and BPP083 GF eluate, purified according to example 9 (Table 17-18). A commercially available FVIII product (ReFacto®, Lot 70591) was used as a reference. Left pane: Silver stained images of gels with BPP079 and BPP083 GF-eluates and ReFacto®. Right pane: Western blot images with BPP083 GF-eluates and ReFacto®.

Conclusion Example 9

The described purification process can be performed in industrial scale in a way, which is reproducible in regard of recovery, purity and product quality. In additional it fulfils the high demand for purity to be able to use the product for treatment of humans.

Example 10

Industrial Scale of Purification Sequence without Specific Affinity Ligand (Anion Multimodal Resin; Capto Adhere Instead)

To study the reproducibility of recovery and purity, purification Steps 2-3 (Capto MMC and SP Sepharose FF) and step 5 (virus inactivation), as described in example 9 were performed for two batches (BPP068-069) in pilot scale. Thereafter the two batches were pooled to one downstream batch (BPP071) and processed according to Step 6-9 in example 9, with the exception that Step 6 (the VIIISelect gel) was exchanged for an anion exchange multi modal chromatography step (Capto Adhere). The whole purification sequence can be studied in Appendix 2. Each batch (BPP068-069) originating from approximately 50 L cell suspension, as described in example 1-2.

The Capto Adhere Step

The anion exchange multi modal column (Capto Adhere, GE Healthcare, Cat. No. 17-5444) was loaded in the range of 5,000-10,000 IU FVIII/mL resin. The gel is before product application equilibrated with equilibration buffer. The virus inactivated solution (as described in example 9, step 5) is loaded to the Capto Adhere column which thereafter is rinsed with equilibration buffer and washed sequentially with wash buffer 1-3 followed by elution of FVIII, as described in Table 20.

TABLE 20

| Multi Modal Chromatography/ Capto Adhere | Equilibration buffer | 0.3 mol/kg NaCl, 0.01 mol/kg $CaCl_2$, 0.01 mol/kg L-histidine, 0.02% Polysorbate 80 (w/w), pH 7 |
|---|---|---|
| | Wash Buffer 1 | 2 mol/kg NaCl, 0.05 mol/kg $CaCl_2$, 0.05 mol/kg L-histidine, 0.02% (w/w) Polysorbate 80, pH 6.5 |
| | Wash Buffer 2 | 0.1 mol/kg NaCl, 0.01 mol/kg $CaCl_2$, 0.01 mol/kg L-histidine, 0.02% (w/w) Polysorbate 80, pH 6.5. |
| | Wash Buffer 3 | 0.3 mol/kg NaCl, 0.01 mol/kg $CaCl_2$, 0.01 mol/kg L-histidine, 0.3 mol/kg L-arginine hydrochloride, 20% (w/w) ethylene glycol, 0.02% Polysorbate 80 (w/w), pH 6.5 |

TABLE 20-continued

| | |
|---|---|
| Elution Buffer | 0.3 mol/kg NaCl, 0.01 mol/kg $CaCl_2$, 0.01 mol/kg L-histidine, 0.8 mol/kg L-arginine hydrochloride, 0.02% Polysorbate 80 (w/w), pH 6.5 |

TABLE 21

Summary of results over the two first chromatography steps (according to example 9, step 2-3) of two pilot scale purification batches.

| | BPP068 | BPP069 |
|---|---|---|
| Starting material (as described in example 1-2) | | |
| Weight (kg) | 98.6 | 110.5 |
| Total FVIII (IU) | 734 570 | 596 700 |
| FVIII yield (%) | 100 | 100 |
| Specific activity* (IU/mg) | 43 | 52 |
| DNA content (pg/ 1000 IU) | $2.1*10^9$ | $7.1*10^8$ |
| Capto MMC eluate (step 2 example 9) | | |
| Weight (kg) | 3.8 | 4.0 |
| Total FVIII (IU) | 500 813 | 389 814 |
| FVIII yield (%) | 68 | 65 |
| Specific activity* (IU/mg) | 449 | 596 |
| DNA content (pg/ 1000 IU) | $3.4*10^7$ | $3.5*10^7$ |
| SP eluate (step 3 example 9) | | |
| Weight (kg) | 2.2 | 3.1 |
| Total FVIII (IU) | 368 903 | 315 000 |
| FVIII yield[1] (%) | 88 | 79 |
| Specific activity* (IU/mg) | 1490 | 2071 |
| DNA content (pg/ 1000 IU) | $1.6*10^7$ | $4.3*10^6$ |

[1] Yield calculated over the SP step
*Measured with Bradford

TABLE 22

Summary of results over the chromatography steps (step 5 - example 9, Capto Adhere, step 8-9 - example 9) in the downstream part of one pilot scale purification batch.

| | BPP071 |
|---|---|
| Starting material (step 5 example 9) | |
| Weight (kg) | 5.2 |
| Total FVIII (IU) | 568 326 |
| FVIII yield (%) | 100 |
| Specific activity (IU/mg) | — |
| DNA content (pg/ 1000 IU) | — |
| Capto Adhere eluate | |
| Weight (g) | 296 |
| Total FVIII (IU) | 543 752 |
| FVIII yield [2] (%) | 96 |
| Specific activity * (IU/mg) | 5117 |
| DNA content (pg/ 1000 IU) | $2.5*10^5$ |
| Q eluate (step 8, example 9) | |
| Weight (g) | 244 |
| Total FVIII (IU) | 266212 |
| FVIII yield [3] (%) | 52 |
| Specific activity (IU/mg) | — |
| DNA content (pg/ 1000 IU) | 1121 |
| GF eluate (step 9, example 9) | |
| Weight (g) | 12 |
| Total FVIII (IU) | 5610 |
| FVIII yield [4] (%) | 84 |
| Specific activity * (IU/mg) | 8061 |
| DNA content (pg/ 1000 IU) | 836 |

Figure 6:
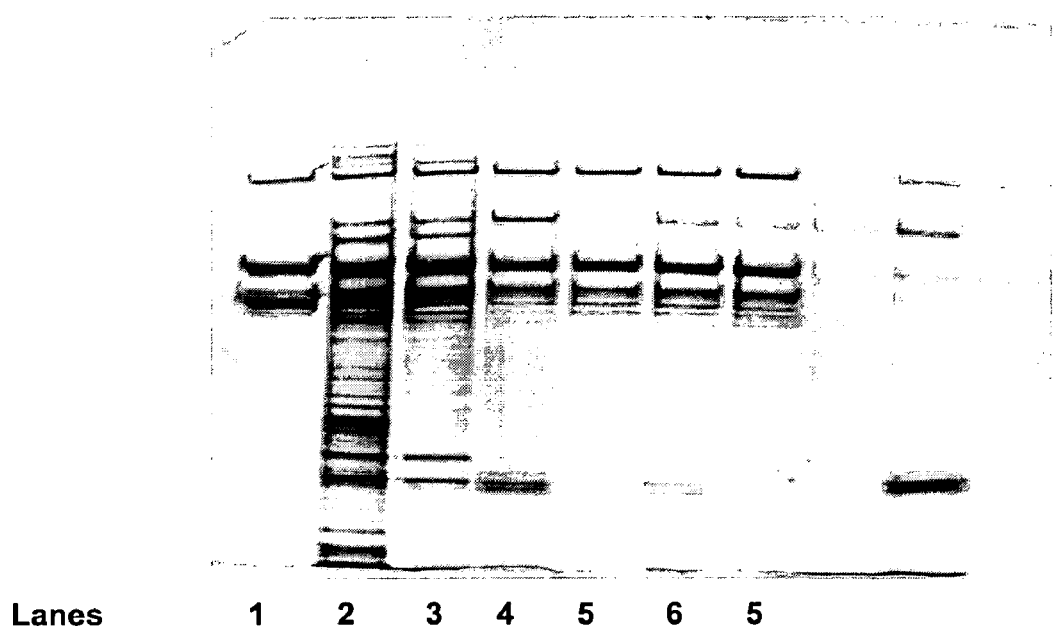

[2] Yield calculated over the Capto Adhere step
[3] Yield calculated over the Q Sepharose step
[4] Yield calculated over the Gel filtration step
* Measured with Bradford FIG. 6 shows a SDS-PAGE silver staining gel of samples from pilot batch BPP071 purified according to example 10. Lane 1 shows a commercially available FVIII product (ReFacto®). Lane 2 shows the starting material (SP-filtrate) before the Capto Adhere Step. Lane 3 shows the purity profile of the Capto Adhere eluate. Lane 4 shows the purity after the purification sequence SP filtrate-Capto Adhere-Q Seph. Lane 5 shows the purity after the purification sequence SP filtrate-Capto Adhere-Q Seph-Gel filtration.

Figure 7:
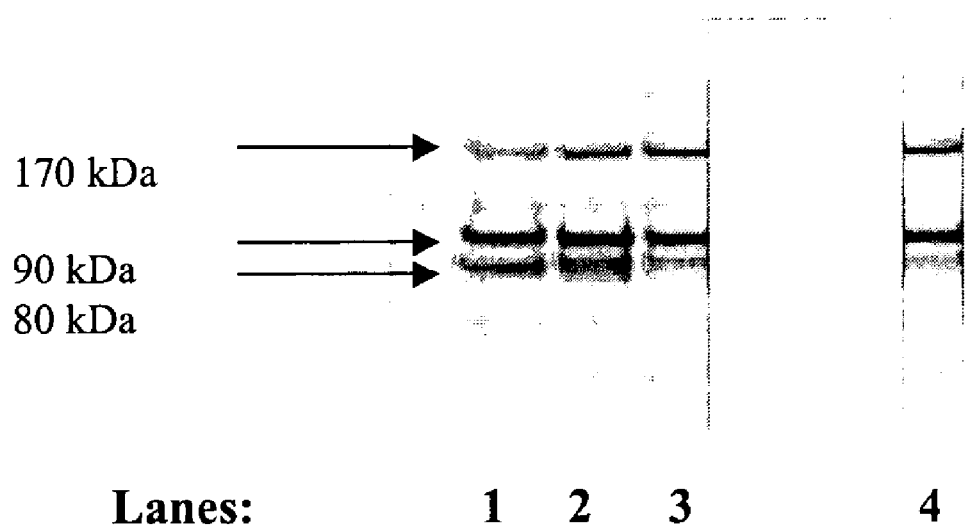

FIG. 7 shows a Western Blot gel of samples from pilot batch BPP071 purified according to example 10. Lane 1 shows a commercially available FVIII product (ReFacto®). Lane 2 shows the Capto Adhere eluat. Lane 3 shows the result of the purification sequence SP filtrate-Capto Adhere-Q Seph. Lane 4 shows the results after the purification sequence SP filtrate-Capto Adhere-Q Seph-Gelfiltration.

Conclusion Example 10

The purification process in pilot scale, including a multi modal chromatography step (Capto Adhere) instead of the VIIISelect affinity ligand, reveals the same recovery, purity and product quality in the final GF-eluate.

Description of Analysis
FVIII: C, Screening Method Based on Coatest

The method is based on the two-stage principle, and was performed using micro plate technique. In stage one, activated factor X (Xa) is generated via the intrinsic pathway where FVIII: C acts as a co-factor. In stage two, Factor Xa is then determined by the use of a synthetic chromogenic substrate, S-2222 in the presence of a thrombin inhibitor 1-2581 to prevent hydrolysis of the substrate by thrombin. The reaction is stopped with acid, and the VIII: C activity, which is proportional to the release of pNA (para-nitroaniline), is determined photo metrically at 405 nm against a reagent blank.

The method complies with the requirements in the European Pharmacopoeia. The unit of FVIII: C is expressed in international units (IU) as defined in the current International Concentrate Standard (IS) established by the World Health Organization (WHO). The routine using buffer containing 1% BSA instead of severe hemophilic plasma for predilutions has been validated. See also literature references (European Pharmacopoeia Supplement 2000, general Methods, 2.7.4. Assay of Blood Coagulation FVIII; Rosén S (1984) Assay of FVIII: C with a Chromogenic Substrate. J, Haematol, Suppl 40, vol 33, 139-145, 1984; Carlebjöork G, Oswaldsson U, Rosén S (1987) A simple and accurate micro plate assay for the determination of FVIII activity. Thrombosis Research 47; 5-14, 1987; Mire-Sluis A R, Gerrard T, Gaines das R, Padilla A and Thorpe R. Biological assays: Their Role in the development and quality Control of Recombinant Biological Medicinal Products. Biological, 24, 351-362 (1996)).

Determination of Total Protein According to Bradford

Protein determination according to Bradford is based on the observation that the absorbance maximum for an acidic solution of Coomassie Brilliant Blue G-250 shifts from 465 nm to 595 nm when binding to protein occurs. Both hydrophobic and ionic interactions stabilize the anionic form of the dye, causing a visible colour change. The assay is useful since the extinction coefficient of a dye-albumin complex solution is constant over a 10-fold concentration range. See also reference Bradford, M M. A rapid and sensitive method for the quantisation of microgram quantities of protein utilizing the principle of protein-dye binding. *Analytical Biochemistry* 72: 248-254. 1976. for further information.

Determination of Total Protein According to Amino Acid Analysis (AAA)

Before the AAA all proteins are hydrolyzed by 6 M HCl for 24 h at 110° C. The amino acids are separated by cation-exchange chromatography on sulphonated polystyrene resins and detected continuously in the eluent. The detection is based on post-column ninhydrin derivatisation using a dual photometer for simultaneous measurement at 440 nm for proline and hydroxyproline and 570 nm for all other amino acids. The amino acids asparagine and glutamine are both deamidated during AAA and are determined as aspartic acid and glutamic acid, respectively. Thus, the results of aspartic acid and glutamic acid represent the sum of aspartic acid/asparagine (Asx) and glutamic acid/glutamine (Glx), respectively, in the original sample. Tryptophan is not generating a distinct response using this method, and, thus, is not quantified by the AAA. Cysteine is destroyed during the hydrolysis and is not quantified. The AAA is further described in reference: Total protein AAA analytical method. Spackman, D. H., Stein, W. H., and Moore, S. (1958) Anal. Biochem. 30: 1190-1206.

Purity or Specific Activity (FVIII:C/Total Protein)

The purity (or also called specific activity) for a sample, is calculated taking the value achieved from the FVIII:C analysis and divide it with the value achieved from the analysis of total protein.

SDS-PAGE (Molecular Weight Distribution)

SDS polyacrylamide gel electrophoresis (SDS-PAGE) involves the separation of proteins based on their size. This method describes the SDS-PAGE of proteins, which is run under reduced conditions. By heating the sample under denaturing and reducing conditions, proteins become unfolded and coated with anionic detergent sodium dodecyl sulphate (SDS), acquiring a high net negative charge that is proportional to the length of the polypeptide chain. When loaded onto a polyacrylamide gel matrix and placed in an electric field, the negatively charged protein molecules migrate towards the positively charged electrode and are separated by a molecular sieving effect, i.e. by their molecular weight. Polyacrylamide gels restrain larger molecules from migrating as fast as smaller molecules. Because the charge-to-mass ratio is nearly the same among SDS-denatured polypeptides, the final separation of proteins is dependent almost entirely on the differences in relative molecular mass of polypeptides. In a gel of uniform density the relative migration distance of a protein ($R_f$) is negatively proportional to the log of its mass. If proteins of known mass are run simultaneously with the unknowns, the relationship between Rf and mass can be plotted, and the masses of unknown proteins estimated. The protein bands separated by electrophoresis are visualized by silver staining. Evaluation is done visually by judging the appearances of the standards, reference (control sample) and analysed samples.

DNA Analytical Method (Quantitative Polymerase Chain Reaction, qPCR)

The assay is a real time quantitative PCR (qPCR) assay based on SYBR Green 1 chemistry. It is based on a publication of Umetani et al. with some added improvements (Umetani N, Kim J, Hiramatzu S, Reber H A, Hines O J, Bilchik A J and Hoon D S B. Increased Integrity of Free Circulating DNA in Sera of Patients with Colorectal or Periampullary Cancer: Direct Quantitative PCR for ALU Repeats. Clin Chem 2006; 52:1062-1069). During each PCR cycle a 115 base pair fragment from the ALU sequence families is amplified by the primers, ALU115-F and ALU115-R. The highly abundant ALU sequence family is limited to genome of the family Homimidae (Chimpanzee, Gorilla, Human and Orang-utan), but the assay only amplify DNA from human origin. The procedure allows for high through put analysis of residual HEK293F DNA in cell free tissue culture media and it's downstream purification processes.

Western Blot, FVIII Molecular Mass Distribution

Proteins and peptides in FVIII preparations are separated according to molecular mass by sodium dodecyl sulphate (SDS) polyacrylamide gel electrophoresis (PAGE) under reducing conditions. Thereafter, the proteins are transferred electrophoretically from the gel matrix to a nitrocellulose membrane which is subsequently incubated with a blocking agent. Polyclonal sheep antibodies directed to the whole FVIII molecule is then added followed by a secondary antibody which is specific for the Fc part of goat/sheep antibodies. As a third step soluble complexes of goat antibody to horseradish peroxidase (HRP) and HRP are added. FVIII polypeptides are then detected by occurrence of blue bands after incubation with the substrate 4-chloro-1-naphtol.

Two Dimension Polyacrylamide Gel Electrophoresis (2-D PAGE)

2-D-PAGE was carried out in order to study the electrophoretic band pattern of the protein chains of Human-cl rhFVIII. Isoelectric focusing was performed as the first dimension run using a linear pH gradient of pH 3 to 10. The second dimension SDS-PAGE was run using polyacrylamide gradient (3-8%) gels. The gels were either stained with silver-stain following the second dimension run or were submitted to western blotting (O' Farrell P H (1975) High resolution two-dimensional electrophoresis of proteins. *J Biol Chem* 250: 4007-4021).

The invention claimed is:

1. A process of purifying or enriching coagulation FVIII employing chromatography comprising the steps of
providing a fraction containing FVIII in an aqueous solution having a high ionic strength;
contacting the fraction containing FVIII with a multimodal resin;
washing the multimodal resin having FVIII adsorbed with an aqueous washing buffer;
eluting FVIII containing fractions by an aqueous elution buffer comprising at least one amino acid which is positively charged at pH 6 to 8, wherein said at least one amino acid is selected from lysine, arginine and histidine or a combination thereof in a concentration between 0.4M and 1M; and
collecting FVIII containing fractions in purified or enriched form.

2. The process of claim 1 wherein the multimodal resin comprises moieties bound to a matrix and the moieties are able to interact with FVIII in an aqueous environment by ionic interactions and other types of interactions such as hydrogen bonding and hydrophobic interaction.

3. The process of claim 1 characterised in that the FVIII is recombinant FVIII, in particular B-domain deleted FVIII.

4. The process of claim 1, characterised in that the aqueous solution comprises FVIII in a high salt solution corresponding to a conductivity of from about 25 to about 200 mS/cm at 25° C.

5. The process of claim 1 characterized in that the elution buffer additionally comprises at least one hydroxyl group containing organic compounds such as an alcohol, at least one amino group containing organic compound, at least one source providing $Ca^{2+}$ ions, at least one compound for regulating the ionic strength of the buffer such as inorganic salts, at least one non-ionic detergent and at least one buffering substance to regulate the pH from about 6 to about 8 in particular to about a neutral value.

6. The process of claim 5, characterised in that the alcohol is selected from the group consisting of methanol, propanol, ethylene glycol and propylene glycol; the source providing $Ca^{2+}$ is $CaCl_2$; the inorganic salts are selected from the group consisting of KCl and NaCl; the non-ionic detergent is selected from the group consisting of Tween 20, Tween 80 and Pluronic F68; the buffering substance is selected from the group consisting of sodium citrate, histidine, HEPES, MES and sodium acetate at a pH between 6-8.

7. The process of claim 5, characterised in that the wash buffer is applied to the multimodal resin, to wash away contaminants and retain FVIII, before the FVIII is released.

8. The process of claim 1, characterised in that the "multimodal" chromatography resin contains at least one of the following moieties:
a. a positively charged N-Benzyl-N-methyl ethanolamine ligand,
b. a negatively charged 2-(benzoylamino) butanoic acid ligand,
c. a phenylpropyl ligand,
d. a N-hexyl ligand,
e. a 4-Mercapto-Ethyl-Pyridine ligand,
f. a 3-((3-methyl-5-((tetrahydrofuran-2-ylmethyl)-amino)-phenyl)-amino)-benzoic acid ligand or combinations thereof.

9. The process of claim 1, characterised in that the "multimodal" chromatography resin is selected from the following commercially available resins HEP Hypercel™; PPA Hypercel™; Capto Adhere™; Capto MMC™; MEP Hypercel™.

10. The process of claim 1, characterised in that the multimodal chromatography step is combined with a FVIII affinity chromatography step wherein the affinity is provided by a ligand which is based on a protein expressed in yeast.

11. The process of claim 1, characterised in that the purification sequence further comprises pathogen removal/inactivation steps comprising a chemically based inactivation step, a size based removal step, chromatography steps or combinations thereof which steps are based on different physiological properties directed to the pathogen to be removed.

12. The process of claim 1, characterised in that the purification sequence further comprises the following steps:
i. an anionic membrane such as Sartobind Q in particular for DNA reduction;
ii. a cation multimodal resin such as Capto MMC;
iii. a cation exchanger resin such as SP Sepharose FF;
iv. an anionic membrane such as Sartobind Q, in particular for further DNA reduction
v. a chemically based inactivation step for lipid enveloped viruses in particular the solvent/detergent-inactivation employing tri-n-butyl phosphate and Triton X-100;
vi. an affinity resin based on a protein ligand such as VIISelect, the VIIISelect ligand consisting of an antibody fragment expressed in yeast or an anion multimodal chromatography resin such as Capto Adhere;
vii. a pathogen filtration removal step with a mean pore size of about 20 nm such as Planova 20N;
viii. an anion exchanger resin such as Q Sepharose FF;
ix. a size exlusion chromatography resin such as Superdex 200 pg.

13. The process of claim 12, characterised in that the elution conditions for FVIII of the cation exchange step is based on Ca, the concentration ranging from 0.15-0.25 M and the total conductivity of the elution buffer not increasing 25 mS/cm at 25° C.

14. The process of claim 12, characterized in that the purity of FVIII after the last purification step is at least 4000 IU/mg, and that the DNA content is less than 1000 pg/1000 IU FVIII.

15. The process of claim 12, characterized in that the purity of FVIII after the last purification step is at least 9000 IU/mg, and that the DNA content is less than 1000 pg/1000 IU FVIII.

16. The process of claim 12, characterized in that the purity of FVIII after the last purification step is at least 10,000 IU/mg, and that the DNA content is less than 1000 pg/1000 IU FVIII.

17. The process of claim 12, characterized in that the purity of FVIII after the last purification step is at least 4000 IU/mg, and that the DNA content is less than 100 pg/1000 IU FVIII.

18. The process of claim 12, characterized in that the purity of FVIII after the last purification step is at least 9000 IU/mg, and that the DNA content is less than 100 pg/1000 IU FVIII.

19. The process of claim 12, characterized in that the purity of FVIII after the last purification step is at least 10,000 IU/mg, and that the DNA content is less than 100 pg/1000 IU FVIII.

20. The process of claim 12, characterized in that the purity of FVIII after the last purification step is at least 4000 IU/mg, and that the DNA content is less than 10 pg/1000 IU FVIII.

21. The process of claim 12, characterized in that the purity of FVIII after the last purification step is at least 9000 IU/mg, and that the DNA content is less than 10 pg/1000 IU FVIII.

22. The process of claim 12, characterized in that the purity of FVIII after the last purification step is at least 10,000 IU/mg, and that the DNA content is less than 10 pg/1000 IU FVIII.

* * * * *